(12) United States Patent
Yasumura

(10) Patent No.: US 10,577,313 B2
(45) Date of Patent: Mar. 3, 2020

(54) METHOD FOR PRODUCING SULFOXIDE DERIVATIVE

(71) Applicant: KUMIAI CHEMICAL INDUSTRY CO., LTD., Tokyo (JP)

(72) Inventor: Shingo Yasumura, Shizuoka (JP)

(73) Assignee: KUMIAI CHEMICAL INDUSTRY CO., LTD., Tokyo (JP)

( * ) Notice: Subject to any disclaimer, the term of this patent is extended or adjusted under 35 U.S.C. 154(b) by 0 days.

(21) Appl. No.: 16/080,923

(22) PCT Filed: Feb. 28, 2017

(86) PCT No.: PCT/JP2017/007595
§ 371 (c)(1),
(2) Date: Aug. 29, 2018

(87) PCT Pub. No.: WO2017/150478
PCT Pub. Date: Sep. 8, 2017

(65) Prior Publication Data
US 2019/0062269 A1   Feb. 28, 2019

(30) Foreign Application Priority Data
Mar. 3, 2016 (JP) ................................. 2016-040728

(51) Int. Cl.
| C07C 315/02 | (2006.01) |
| B01J 31/22 | (2006.01) |
| C07F 15/02 | (2006.01) |
| C07F 1/04 | (2006.01) |
| C07B 45/04 | (2006.01) |
| C07C 317/22 | (2006.01) |
| C07C 319/20 | (2006.01) |
| C07C 323/12 | (2006.01) |
| C07B 61/00 | (2006.01) |

(52) U.S. Cl.
CPC ............ C07C 315/02 (2013.01); C07B 45/04 (2013.01); C07C 317/22 (2013.01); C07C 319/20 (2013.01); C07C 323/12 (2013.01); B01J 31/22 (2013.01); B01J 31/2282 (2013.01); C07B 61/00 (2013.01)

(58) Field of Classification Search
CPC ....... B01J 31/22; B01J 31/2282; C07B 61/00; C07B 45/04; C07C 315/02; C07C 319/20
See application file for complete search history.

(56) References Cited

U.S. PATENT DOCUMENTS

2015/0087833 A1* 3/2015 Domon .................. A01N 31/16
544/335

FOREIGN PATENT DOCUMENTS

WO    WO-2016076160 A1 *  5/2016 ........... C07C 315/02

OTHER PUBLICATIONS

Legros et al. ("Investigations on the Iron-Catalyzed Asymmetric Sulfide Oxidation", Chemistry: A European Journal, vol. 11, Issue 4, Feb. 4, 2005, pp. 1086-1092).*

* cited by examiner

Primary Examiner — Rosalynd A Keys
(74) Attorney, Agent, or Firm — Wenderoth, Lind & Ponack, L.L.P.

(57) ABSTRACT

A method for producing a sulfoxide derivative represented by general formula (1),

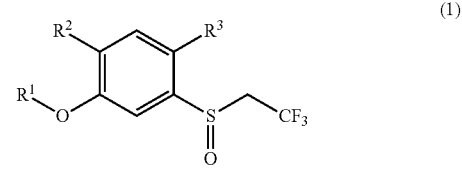

the method being characterized in that a sulfide derivative represented by general formula (2)

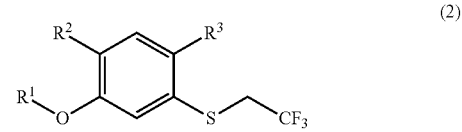

is reacted with an oxidizing agent in the presence of a catalyst that is a metal-ligand complex containing a metal compound and, as a ligand, a compound represented by general formula (3),

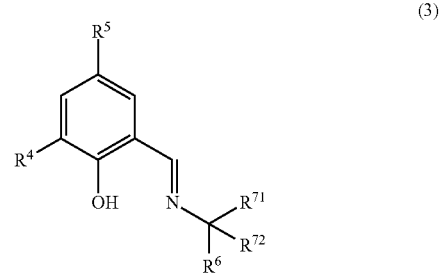

and in the presence of a benzoic acid compound represented by general formula (4)

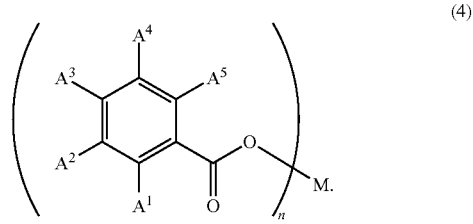

14 Claims, No Drawings

METHOD FOR PRODUCING SULFOXIDE DERIVATIVE

TECHNICAL FIELD

The present invention relates to a method for producing a sulfoxide derivative.

BACKGROUND ART

Sulfoxide derivatives have attracted attention in the field of agricultural chemicals etc. (see Patent document 1). It is therefore important that sulfoxide derivatives are produced selectively and in high yields. Oxidation of sulfide derivatives is known as a method for producing sulfoxide derivatives. However, in general, this method has a problem that a sulfone derivative which is an excessively oxidized product is by-produced. The unnecessary by-produced sulfone derivative lowers the yield of the desired sulfoxide derivative. Furthermore, since the physical properties of both derivatives are similar, it is difficult to obtain a purified target sulfoxide derivative in the industrial production by removing the byproduct sulfone derivative from the crude product after the oxidation reaction. That is to say it is difficult to separate and purify the target product with high yield on an industrial scale. Accordingly, it has been desired to be able to selectively produce sulfoxide derivatives by avoiding excessive oxidation to sulfone derivatives.

Patent Document 1 discloses that a sulfoxide derivative can be produced by an oxidation reaction with metachloroperbenzoic acid (See, for example, Examples 13 and 27 of Patent Document 1). However, considering the environmental aspect, the use of metachloroperbenzoic acid is not favorable for industrial production. The reasons are as follows. After the reaction, the metachloroperbenzoic acid becomes methachlorobenzoic acid as a waste. As a result, the use of metachloroperbenzoic acid places a heavy burden on the environment. In addition, since metachloroperbenzoic acid is expensive, the method of using metachloroperbenzoic acid is industrially undesirable.

On the other hand, oxidation using hydrogen peroxide is an industrially preferable and useful method. The reasons are as follows. Since hydrogen peroxide becomes harmless water after the reaction, it is environmentally friendly. Furthermore, hydrogen peroxide is industrially cheap.

Non-patent document 1 discloses asymmetric oxidation from a sulfide derivative to an optically active sulfoxide derivative. Non-Patent document 1 discloses a method using a Schiff base, which is conventionally known as a ligand and a benzoic acid compound. It has also been reported that this method gives some yield. However, the method described in Non-Patent Document 1 requires further improvement in yield. In addition, Non-Patent Document 1 describes that the yield and the enantiomeric excess ratio change depending on the substituent of the aryl moiety of the arylalkyl sulfide derivative. However, Non-Patent Document 1 merely discloses the yield and the enantiomeric excess ratio when the substituent is limited. In other words, Non-Patent Document 1 does not disclose a method for producing titled compound of the present invention, by which titled compound of the present invention can be obtained in sufficient and satisfactory yield and the like.

From the viewpoints of yield and enantiomeric excess ratio, it has been reported that 4-methoxybenzoic acid alkali metal salt and 4-(N,N-dimethylamino) benzoic acid alkali metal salt are excellent as benzoic acid compounds. Furthermore, the Schiff bases of the ligands are reported as follows. Regarding the amine moiety of Schiff's base as a ligand, tert-leucinol was superior to valinol from the viewpoint of yield and enantiomeric excess ratio. Regarding the salicylaldehyde moiety of Schiff's base as a ligand, 3,5-diiodosalicylaldehyde and 3,5-dibromosalicylaldehyde were superior to unsubstituted salicylaldehyde from the same viewpoint as above (see Non-Patent document 1, Table 1). However, in the production of titled compound of the present invention, it has not been known whether these benzoic acid compounds and ligands have an industrially advantageous effect. Furthermore, from the viewpoint of difficulty of availability, difficulty in industrial production, and/or cost, the use of 3,5-diiodosalicylaldehyde as a salicylaldehyde moiety of Schiff's base as a ligand is industrially undesirable.

PRIOR ART DOCUMENT

Patent Document

Patent Document 1: International Publication No. 2013/157229

Non-Patent Document

Non-Patent Document 1: Chem. Eur. J., 2005, 11, 1086-1092

SUMMARY OF THE INVENTION

Subject to be Solved by the Invention

There has been an urgent need for a method for producing sulfoxide derivatives, which can solve one or more of the above mentioned disadvantages or problems in the prior art.

Accordingly, an object of the present invention is to provide a method for producing a sulfoxide derivative, which is industrially favorable, economical and environmentally friendly.

A more specific object of the present invention is to provide a method capable of producing sulfoxide derivative selectively and in high yield. To achieve this goal, it is necessary to provide a controlled oxidation reaction from the sulfide derivative to the sulfoxide derivative in order to avoid over oxidation to the sulfone derivative.

It is another more specific object of the present invention to provide a method, which is inexpensive and can reduce the environmental burden.

For example, one of the specific objects of the present invention is to provide a method for producing sulfoxide derivatives using hydrogen peroxide, which attracts attention as a clean and excellent oxidizing agent without using metachloroperbenzoic acid as oxidizing agent.

Furthermore, an inexpensive compound is preferable as the ligand of the catalyst used in the oxidation reaction. For example, as a substituent on a benzene ring in a ligand, a chlorine atom is acceptable, but an iodine atom is not preferable because it is expensive. In other words, as a salicylaldehyde moiety of Schiff's base as a ligand, it is desired to use industrially preferable salicylaldehyde derivatives without using salicylaldehyde derivatives having the above-mentioned disadvantages such as 3,5-diiodosalicylaldehyde.

Solution to the Problem

In view of the situation as described above, the inventor of the present invention has conducted intensive studies on a method for producing a sulfoxide derivative. As a result, the present inventor has unexpectedly found that the sulfoxide derivative represented by general formula (1):

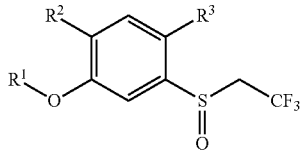

(wherein, $R^1$, $R^2$ and $R^3$ are as described below), can be produced by reacting a sulfide derivative represented by general formula (2):

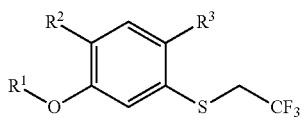

(wherein, $R^1$, $R^2$ and $R^3$ are as defined below), with an oxidizing agent in the presence of both a catalyst which is a metal-ligand complex containing a metal compound and a ligand compound represented by general formula (3):

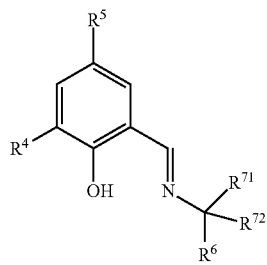

(wherein, $R^4$, $R^5$, $R^6$, $R^{71}$ and $R^{72}$ are as described below), and a benzoic acid compound represented by general formula (4):

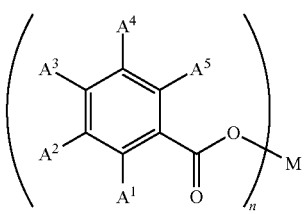

(wherein, $A^1$, $A^2$, $A^3$, $A^4$, $A^5$, M and n are as described below). Based on this finding, the present inventor has completed the present invention.

That is, the present invention has solved the above-mentioned problems by providing the inventions described in the following [1] to [21].

[1] A method for producing a sulfoxide derivative represented by general formula (1):

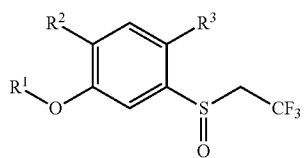

(wherein, $R^1$ is a C1 to C10 alkyl group, a C3 to C6 cycloalkyl C1 to C6 alkyl group, wherein the said C3 to C6 cycloalkyl group moiety may be monosubstituted or polysubstituted by a halogen atom, a C1 to C4 alkyl group, a C1 to C4 alkoxy group or C1 to C4 haloalkyl group, a phenyl C1 to C6 alkyl group, wherein the said phenyl group moiety may be monosubstituted or polysubstituted by a halogen atom, a C1 to C4 alkyl group, a C1 to C4 alkoxy group, a C1 to C6 haloalkyl group, a cyano group or a nitro group, a C1 to C4 alkoxy C2 to C10 alkyl group, a C1 to C4 haloalkoxy C2 to C10 alkyl group, a C1 to C4 alkylthio C2 to C10 alkyl group, a C1 to C4 alkylsulfinyl C2 to C10 alkyl group, a C1 to C4 alkyl sulfonyl C2 to C10 alkyl group, a C1 to C4 haloalkylthio C2 to C10 alkyl group, a C1 to C4 haloalkylsulfinyl C2 to C10 alkyl group, a C1 to C4 haloalkylsulfonyl C2 to C10 alkyl group, a C1 to C6 haloalkyl group, a C3 to C6 cycloalkyl C1 to C6 haloalkyl group wherein the said C3 to C6 cycloalkyl group moiety may be monosubstituted or polysubstituted by a halogen atom, a C1 to C4 alkyl group, a C1 to C4 alkoxy group or a C1 to C6 haloalkyl group, a phenyl C1 to C6 haloalkyl group, wherein the said phenyl moiety may be monosubstituted or polysubstituted by a halogen atom, a C1 to C4 alkyl group, a C1 to C4 alkoxy group, a C1 to C4 haloalkyl group, a cyano group or a nitro group, or a C1 to C4 haloalkylthio C1 to C6 haloalkyl group;

$R^2$ and $R^3$ are each independently a hydrogen atom, a halogen atom or a C1 to C4 alkyl group), which comprises reacting a sulfide derivative represented by general formula (2):

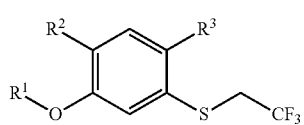

(wherein, $R^1$, $R^2$ and $R^3$ are as defined above), with an oxidizing agent in the presence of both a catalyst which is a metal-ligand complex containing a metal compound and a ligand compound represented by general formula (3):

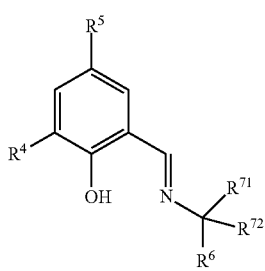

(3)

(wherein, $R^4$ and $R^5$ are each independently a hydrogen atom, a halogen atom, a C1 to C6 alkyl group, a phenyl C1 to C6 alkyl group, a C6 to C10 aryl group, a cyano group, a nitro group or a C1 to C6 alkoxy group;
$R^6$ is a C1 to C4 alkyl group, a cyano group, a nitro group, a carboxy group, a C1 to C4 alkoxycarbonyl group, a C1 to C4 alkylcarbonyl group, a hydroxy C1 to C4 alkyl group, a C1 to C4 alkoxy C1 to C4 alkyl group, an amino C1 to C4 alkyl group, a cyano C1 to C4 alkyl group, a nitro C1 to C4 alkyl group, a carboxy C1 to C4 alkyl group or a C1 to C4 alkoxy carbonyl C1 to C4 alkyl group;
$R^{71}$ and $R^{72}$ are each independently a hydrogen atom, a C1 to C6 alkyl group, a phenyl C1 to C6 alkyl group or a C6 to C10 aryl group, provided that the case where both $R^{71}$ and $R^{72}$ are hydrogen atoms is excluded.), and
a benzoic acid compound represented by the following formula (4):

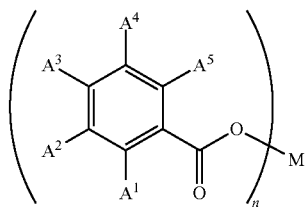

(4)

(wherein, $A^1$ is a C1 to C2 alkoxy group;
$A^2$ is a hydrogen atom;
$A^3$ is a hydrogen atom or a C1 to C2 alkoxy group;
$A^4$ is a hydrogen atom;
$A^5$ is a C1 to C2 alkoxy group;
M is a hydrogen atom, an alkali metal atom or an alkaline earth metal atom; and n is 1 or 2).

[2] The method according to [1], wherein
$R^1$ is a C1 to C10 alkyl group,
a C3 to C6 cycloalkyl C1 to C6 alkyl group, wherein the said C3 to C6 cycloalkyl group moiety may be monosubstituted or polysubstituted by a halogen atom or a C1 to C4 alkyl group,
a phenyl C1 to C6 alkyl group, wherein the said phenyl group moiety may be monosubstituted or polysubstituted by a halogen atom or a C1 to C4 alkyl group,
a C1 to C4 alkoxy C2 to C10 alkyl group,
a C1 to C4 haloalkoxy C2 to C10 alkyl group,
a C1 to C4 alkylthio C2 to C10 alkyl group,
a C1 to C4 alkylsulfinyl C2 to C10 alkyl group,
a C1 to C4 alkyl sulfonyl C2 to C10 alkyl group,
a C1 to C4 haloalkylthio C2 to C10 alkyl group,
a C1 to C4 haloalkylsulfinyl C2 to C10 alkyl group,
a C1 to C4 haloalkylsulfonyl C2 to C10 alkyl group,
a C1 to C6 haloalkyl group,
a C3 to C6 cycloalkyl C1 to C6 haloalkyl group wherein the said C3 to C6 cycloalkyl group moiety may be monosubstituted or polysubstituted by a halogen atom or a C1 to C4 alkyl group or a phenyl C1 to C6 haloalkyl group, wherein the said phenyl group moiety may be monosubstituted or polysubstituted by a halogen atom or a C1 to C4 alkyl group.

[3] The method according to [1], wherein
$R^1$ is a C1 to C10 alkyl group,
a C1 to C4 alkoxy C2 to C10 alkyl group,
a C1 to C4 haloalkoxy C2 to C10 alkyl group,
a C1 to C4 alkylthio C2 to C10 alkyl group,
a C1 to C4 alkylsulfinyl C2 to C10 alkyl group,
a C1 to C4 alkyl sulfonyl C2 to C10 alkyl group,
a C1 to C4 haloalkylthio C2 to C10 alkyl group,
a C1 to C4 haloalkylsulfinyl C2 to C10 alkyl group,
a C1 to C4 haloalkylsulfonyl C2 to C10 alkyl group, or
a C1-C6 haloalkyl group.

[4] The method according to [1], wherein $R^1$ is a C1 to C4 haloalkylthio C2 to C10 alkyl group; and $R^2$ and $R^3$ are each independently a halogen atom or a C1 to C4 alkyl group.

[5] The method according to [1], wherein $R^1$ is a 5-trifluoromethylthiopentyl group or a 6-trifluoromethylthiohexyl group; and either $R^2$ is a fluorine atom and $R^3$ is a chlorine atom, or $R^2$ and $R^3$ are methyl groups.

[6] The method according to [1], wherein $R^1$ is a 5-trifluoromethylthiopentyl group; $R^2$ is a fluorine atom; and $R^3$ is a chlorine atom.

[7] The method according to [1], wherein $R^1$ is a 6-trifluoromethylthiohexyl group; and $R^2$ and $R^3$ are methyl groups.

[8] The method according to any one of [1] to [7], wherein the metal compound is an iron compound;
$R^4$ is a hydrogen atom;
$R^5$ is a hydrogen atom or a halogen atom;
$R^6$ is a hydroxymethyl group; and
$R^{71}$ and $R^{72}$ are each independently a hydrogen atom or a C1 to C6 alkyl group, provided that the case where both $R^{71}$ and $R^{72}$ are hydrogen atoms is excluded.

[9] The method according to any one of [1] to [7], wherein the metal compound is an iron compound;
$R^4$ is a hydrogen atom;
$R^5$ is a hydrogen atom, a chlorine atom or a bromine atom;
$R^6$ is a hydroxymethyl group; and
either $R^{71}$ is a methyl group and $R^{72}$ is a methyl group, or $R^{71}$ is a hydrogen atom and $R^{72}$ is an isopropyl group.

[10] The method according to any one of [1] to [7], wherein the metal compound is an iron compound;
$R^4$ is a hydrogen atom;
$R^5$ is a hydrogen atom or a chlorine atom;
$R^6$ is a hydroxymethyl group; and
either $R^{71}$ is a methyl group and $R^{72}$ is a methyl group, or $R^{71}$ is a hydrogen atom and $R^{72}$ is an isopropyl group.

[11] The method according to any one of [1] to [7], wherein the metal compound is an iron compound;
$R^4$ is a hydrogen atom;
$R^5$ is a hydrogen atom;
$R^6$ is a hydroxymethyl group;
$R^{71}$ is a methyl group; and the $R^{72}$ is a methyl group.

[12] The method according to any one of [1] to [7], wherein the metal compound is an iron compound;
$R^4$ is a hydrogen atom;
$R^5$ is a chlorine atom;
$R^6$ is a hydroxymethyl group;
$R^{71}$ is a methyl group; and $R^{72}$ is a methyl group.

[13] The method according to any one of [1] to [12], wherein M is an alkali metal atom; and n is 1.

[14] The method according to any one of [1] to [12], wherein M is a sodium atom; and n is 1.

[15] The method according to any one of [1] to [12], wherein
$A^1$ is a methoxy group;
$A^2$ is a hydrogen atom;
$A^3$ is a hydrogen atom or a methoxy group;
$A^4$ is a hydrogen atom;
$A^5$ is a methoxy group;
M is a sodium atom; and n is 1.

[16] The method according to any one of [1] to [12], wherein
$A^1$ is a methoxy group;
$A^2$ is a hydrogen atom;
$A^3$ is a hydrogen atom;
$A^4$ is a hydrogen atom;
$A^5$ is a methoxy group;
M is a sodium atom; and n is 1.

[17] The method according to any one of [1] to [12], wherein
$A^1$ is a methoxy group;
$A^2$ is a hydrogen atom;
$A^3$ is a methoxy group;
$A^4$ is a hydrogen atom;
$A^5$ is a methoxy group;
M is a sodium atom; and n is 1.

[18] The method according to any one of [1] to [17], wherein the reaction is carried out at −10° C. to 30° C.

[19] The method according to any one of [1] to [17], wherein the reaction is carried out at −5° C. to 10° C.

[20] The method according to any one of [1] to [19], wherein the reaction yield is 90% to 100%.

[21] The method according to any one of [1] to [19], wherein the reaction yield is 95% to 100%.

Effect of the Invention

According to the present invention, a new and industrially applicable production method for producing a sulfoxide derivative represented by the above general formula (1) useful as an acaricide or the like is provided. According to the present invention, there is provided a method for producing a sulfoxide derivative, which can solve one or more of the above-mentioned drawbacks or problems in the prior art.

According to the present invention, it is possible to selectively produce a desired sulfoxide derivative by avoiding excess oxidation to the sulfone derivative. At the same time, the target sulfoxide derivative can be produced in high yield.

Furthermore, since hydrogen peroxide is used without using metachloroperbenzoic acid as an oxidizing agent, the present invention can reduce the environmental burden.

In addition, the method of the present invention does not require a salicylaldehyde derivative having the aforementioned disadvantages of 3,5-diiodosalicylaldehyde as the salicylaldehyde moiety of the Schiff base as a ligand.

Therefore, the method of the present invention is industrially preferable, economical, and environmentally friendly.

EMBODIMENTS OF THE INVENTION

Hereinafter, the present invention will be described in detail.

The method according to the invention can be shown in the following scheme:

(wherein, $R^1$, $R^2$ and $R^3$ are as defined in [1] above.)

Terms and symbols used in the present specification are described below.

The halogen atom refers to a fluorine atom, a chlorine atom, a bromine atom or an iodine atom. Preferred examples of the halogen atom are fluorine atom and chlorine atom from the viewpoint of usefulness and economy of the product and the like.

Examples of alkali metal atom include lithium atom, sodium atom, potassium atom, rubidium atom and cesium atom, preferably lithium atom, sodium atom, potassium atom and cesium atom, more preferably lithium atom, sodium atom and potassium atom.

Examples of alkaline earth metal atoms include magnesium atoms, calcium atoms, strontium atoms and barium atoms, preferably magnesium atoms, calcium atoms and barium atoms.

"Ca to Cb" means that the number of carbon atoms is from a to b. For example, "C1 to C4" of "C1 to C4 alkyl group" means that the alkyl group has 1 to 4 carbon atoms.

A general term like "alkyl" is understood herein to include both straight and branched chain groups such as butyl and tert-butyl. However, when a specific term such as "butyl group" is used, it is specific for "normal butyl group", ie "n-butyl group". In other words, the specific term "butyl group" means "normal butyl group" of a straight chain group, and branched chain isomers such as "tert-butyl" are specifically mentioned when intended. As another example, "pentyloxy group" means a "normal pentyloxy group" of a straight chain group. As still another example, the "hexyloxy group" means a "normal hexyloxy group" of a straight chain group.

The prefixes "n-", "s-" and "sec-", "i-", "t-" and "tert-", "neo-", "c-" and "cyc-", "o-", "m-", and "p-" have their usual meanings as follows: normal, secondary, iso, tertiary, neo, cyclo, ortho, meta, and para.

In the present specification the following abbreviations are used:
"Me" means a methyl group;
"Et" means an ethyl group;
"Pr" and "n-Pr" mean propyl group (ie, normal propyl group);
"i-Pr" means an isopropyl group;
"Bu" and "n-Bu" mean butyl group (ie, normal butyl group);
"s-Bu" means a sec-butyl group;

"i-Bu" means an isobutyl group;
"t-Bu" means a tert-butyl group;
"Ph" means a phenyl group;
"Bn" means a benzyl group.

As used herein, the term "may be monosubstituted" or "monosubstituted" means that one hydrogen atom on the functional group of the subject is substituted by a substituent selected from the designated substituents.

As used herein, the term "may be poly-substituted" or "poly-substituted" means that at least two hydrogen atoms on a functional group of the subject (for example, in one embodiment 2 to 5 hydrogen atoms. In another embodiment 2 to 3 hydrogen atoms) are substituted with the same or different substituents independently selected from the designated substituents.

Definitions and examples of functional groups used in the present specification are described below.

C1 to C10 alkyl group means a straight-chain or branched alkyl group having 1 to 10 carbon atoms.

Examples of C1 to C10 alkyl groups include, but are not limited to, methyl group, ethyl group, propyl group, isopropyl group, butyl group, sec-butyl group, isobutyl group, tert-butyl group, pentyl group, hexyl group, heptyl group, octyl group, nonyl group, decyl group etc.

C2 to C10 alkyl group means a straight-chain or branched alkyl group having 2 to 10 carbon atoms.

Examples of C2 to C10 alkyl groups include, but are not limited to, the appropriate examples of the above C1 to C10 alkyl groups.

C1 to C6 alkyl group means a straight-chain or branched alkyl group having 1 to 6 carbon atoms.

Examples of C1 to C6 alkyl groups include, but are not limited to, the appropriate examples of the above C1 to C10 alkyl groups.

C1 to C4 alkyl group means a straight-chain or branched alkyl group having 1 to 4 carbon atoms.

Examples of C1 to C4 alkyl groups are appropriate examples of the above C1 to C10 alkyl groups.

C1 to C2 alkyl group means a straight chain alkyl group having 1 to 2 carbon atoms.

Examples of C1 to C2 alkyl groups are methyl group and ethyl group.

Haloalkyl group means a linear or branched alkyl group substituted with the same or different one or more halogen atoms.

C1 to C6 haloalkyl group means a linear or branched alkyl group having 1 to 6 carbon atoms which is substituted by the same or different 1 to 13 halogen atoms (wherein the halogen atom has the same meaning as defined above).

Examples of C1 to C6 haloalkyl group include, but are not limited to, fluoromethyl group, difluoromethyl group, trifluoromethyl group, chlorodifluoromethyl group, 2-fluoroethyl group, 2-chloroethyl group, 2-bromoethyl group, 2,2-difluoroethyl group, 2,2,2-trifluoroethyl group, pentafluoroethyl group, 3-fluoropropyl group, 3-chloropropyl group, 3-bromopropyl group, 2,2,3,3,3-pentafluoropropyl group, 2,2,2-trifluoro-1-trifluoromethylethyl group, heptafluoropropyl group, 1,2,2,2-tetrafluoro-1-trifluoromethyl ethyl group, 4-fluorobutyl group, 4-chlorobutyl group, 4-bromobutyl group, 2,2,3,3,4,4,4-heptafluorobutyl group, 5-fluoropentyl group, 5-chloropentyl group, 5-bromopentyl group, 5-iodopentyl group, 6-fluorohexyl group, 6-chlorohexyl group, 6-bromohexyl group, 6-iodohexyl group and the like.

C1 to C4 haloalkyl group means a straight-chain or branched alkyl group having 1 to 4 carbon atoms which is substituted by the same or different 1 to 9 halogen atoms (wherein the halogen atom has the same meaning as defined above).

Examples of C1 to C4 haloalkyl groups include, but are not limited to, the appropriate examples of the above C1 to C6 haloalkyl groups.

C1 to C6 alkoxy group means a (C1 to C6 alkyl) —O— group (wherein the C1-C6 alkyl group moiety has the same meaning as defined above).

Examples of C1 to C6 alkoxy groups include, but are not limited to, a methoxy group, an ethoxy group, a propoxy group, an isopropoxy group, a butoxy group, a sec-butoxy group, an isobutoxy group, a tert-butoxy group, a pentyloxy group, an isopentyloxy group, a hexyloxy group, an isohexyloxy groups and the like.

C1 to C4 alkoxy group means a (C1 to C4 alkyl) —O— group (wherein the C1 to C4 alkyl group has the same meaning as defined above).

Examples of C1 to C4 alkoxy groups are appropriate examples of the above C1 to C6 alkoxy groups.

C1 to C2 alkoxy group means a (C1 to C2 alkyl) —O— group (wherein the C 1 to C2 alkyl group has the same meaning as defined above).

Examples of C1 to C2 alkoxy groups are methoxy and ethoxy groups.

The C1 to C6 haloalkoxy group means a (C1 to C6 haloalkyl) —O— group (wherein the C1-C6 haloalkyl group moiety has the same meaning as above).

Examples of C1 to C6 haloalkoxy group include, but are not limited to, fluoromethoxy group, difluoromethoxy group, trifluoromethoxy group, chlorodifluoromethoxy group, 2-fluoroethoxy group, 2-chloroethoxy group, 2-bromoethoxy group, 2,2-difluoroethoxy group, 2,2,2-trifluoroethoxy group, pentafluoroethoxy group, 3-fluoropropoxy group, 3-chloropropoxy group, 3-bromopropoxy group, 2,2,3,3,3-pentafluoropropoxy group, 2,2,2-trifluoro-1-trifluoromethyl ethoxy group, heptafluoropropoxy group, 1,2,2,2-tetrafluoro-1-trifluoromethyl ethoxy group, 4-fluorobutoxy group, 4-chlorobutoxy group, 4-bromobutoxy group, 2,2,3,3,4,4,4-heptafluorobutoxy group, 5-fluoropentyloxy group, 5-chloropentyloxy group, 5-bromopentyloxy group, 5odopentyloxy group, 6-fluorohexyloxy group, 6-chlorohexyloxy group, 6-bromohexyloxy group, 6-iodohexyloxy group and the like.

C1 to C4 haloalkoxy group means a (C1 to C4 haloalkyl) —O— group (wherein the C1 to C4 haloalkyl group moiety has the same meaning as above).

Examples of the C1 to C4 haloalkoxy group include, but are not limited to, fluoromethoxy group, difluoromethoxy group, trifluoromethoxy group, chlorodifluoromethoxy group, 2-fluoroethoxy group, 2-chloroethoxy group, 2,2,2-trifluoroethoxy group, pentafluoroethoxy group, 3-fluoropropoxy group, 3-chloropropoxy group, 2,2,3,3,3-pentafluoropropoxy group, heptafluoropropoxy group, 2,2,2-trifluoro-1-trifluoromethyl ethoxy group, 4-fluorobutoxy group, 2,2,3,3,4,4,4-heptafluorobutoxy group and the like.

C1 to C4 alkylthio group means a (C1 to C4 alkyl) —S— group (wherein the C1 to C4 alkyl group moiety has the same meaning as described above).

Examples of the C1 to C4 alkylthio group include a methylthio group, an ethylthio group, a propylthio group, an isopropylthio group, a butylthio group, a sec-butylthio group, an isobutylthio group, and a tert-butylthio group.

C1 to C4 haloalkylthio group means a (C1 to C4 haloalkyl) —S— group (wherein the C1 to C4 haloalkyl group moiety has the same meaning as above).

Examples of C1 to C4 haloalkylthio group include, but are not limited to, fluoromethylthio group, difluoromethylthio group, trifluoromethylthio group, chlorodifluoromethylthio group, 2-fluoroethylthio group, 2-chloroethylthio group, 2,2,2-trifluoroethylthio group, pentafluoroethylthio group, 3-fluoropropylthio group, 3-chloropropylthio group, 2,2,3,3,3-pentafluoropropylthio group, heptafluoropropylthio group, 2,2,2-trifluoro-1-trifluoromethylethylthio group, 4-fluorobutylthio group, 2,2,3,3,4,4,4-heptafluorobutylthio group and the like.

C1 to C4 alkylsulfinyl group means a (C1 to C4 alkyl)—SO— group (wherein the C1 to C4 alkyl group moiety has the same meaning as described above).

Examples of the C1 to C4 alkylsulfinyl group include a methylsulfinyl group, an ethylsulfinyl group, a propylsulfinyl group, an isopropylsulfinyl group, a butylsulfinyl group, a sec-butylsulfinyl group, an isobutylsulfinyl group, and a tert-butylsulfinyl group.

C1 to C4 haloalkylsulfinyl group means a (C1-C4 haloalkyl) —SO— group (wherein the C1to C4 haloalkyl group moiety has the same meaning as above).

Examples of the C1 to C4 haloalkylsulfinyl group include, but are not limited to, fluoromethylsulfinyl group, difluoromethylsulfinyl group, trifluoromethylsulfinyl group, chlorodifluoromethyl sulfinyl group, 2-fluoroethyl sulfinyl group, 2-chloroethyl sulfinyl group, 2,2,2-trifluoroethyl sulfinyl group, pentafluoro ethyl sulfinyl group, 3-fluoropropyl sulfinyl group, 3-chloropropyl sulfinyl group, 2,2,3,3,3-pentafluoropropyl sulfinyl group, heptafluoropropyl sulfinyl group, 2,2,2-trifluoro-1-trifluoromethylethyl sulfinyl group, 4-fluorobutyl sulfinyl group, 2,2,3,3,4,4,4-heptafluorobutylsulfinyl group, and the like.

C1 to C4 alkylsulfonyl group means a (C1 to C4 alkyl)—SO$_2$— group (wherein the C1 to C4 alkyl group moiety has the same meaning as described above).

Examples of C1 to C4 alkylsulfonyl group include a methylsulfonyl group, an ethylsulfonyl group, a propylsulfonyl group, an isopropylsulfonyl group, a butylsulfonyl group, a sec-butylsulfonyl group, an isobutylsulfonyl group and a tert-butylsulfonyl group.

C1 to C4 haloalkylsulfonyl group means a (C1 to C4 haloalkyl) —SO$_2$— group (wherein the C1 to C4 haloalkyl group moiety has the same meaning as above).

Examples of C1 to C4 haloalkylsulfonyl group include, but are not limited to, a fluoromethylsulfonyl group, a difluoromethylsulfonyl group, a trifluoromethylsulfonyl group, a chlorodifluoromethylsulfonyl group, a 2-fluoroethylsulfonyl group, a 2-chloroethylsulfonyl group, a 2,2,2-trifluoroethylsulfonyl group, a pentafluoroethylsulfonyl group, a 3-fluoropropylsulfonyl group, a 3-chloropropylsulfonyl group, a 2,2,3,3,3-pentafluoropropylsulfonyl group, a heptafluoropropylsulfonyl group, a 2,2,2-trifluoro-1-trifluoromethyl ethyl sulfonyl group, a 4-fluorobutyl sulfonyl group, 2,2,3,3,4,4,4-heptafluorobutylsulfonyl group and the like.

C3 to C6 cycloalkyl group means a cycloalkyl group having 3 to 6 carbon atoms.

Examples of C3 to C6 cycloalkyl groups include, but are not limited to, cyclopropyl group, cyclobutyl group, cyclopentyl group, cyclohexyl group and the like.

C3 to C6 cycloalkyl C1 to C6 alkyl group means a C1 to C6 alkyl group substituted by a C3 to C6 cycloalkyl group (wherein the C3 to C6 cycloalkyl group moiety and the C1 to C6 alkyl group moiety have the same meaning as defined above).

Examples of C3 to C6 cycloalkyl C1 to C6 alkyl groups include, but are not limited to, cyclopropylmethyl group, 2-cyclopropylethyl group, 3-cyclopropylpropyl group, 4-cyclopropylbutyl group, 5-cyclopropylpentyl group, 6-cyclopropylhexyl group, cyclobutylmethyl group, cyclopentylmethyl group, cyclohexylmethyl group 2-cyclohexylethyl group and the like.

Examples of "C3 to C6 cycloalkyl C1 to C6 alkyl group, wherein the said C3 to C6 cycloalkyl group moiety may be monosubstituted or polysubstituted by a halogen atom, a C1 to C4 alkyl group, C1 to C4 alkoxy group or a C1 to C4 haloalkyl group" are C3 to C6 cycloalkyl C1 to C6 alkyl groups as described above and examples of 2-(2,2-difluorocyclopropyl) ethyl group, 2-(4,4-difluorocyclohexyl) ethyl group, 2-(4-tert-butylcyclohexyl) ethyl group, 2-(4-methoxycyclohexyl) ethyl group, 2-(4-trifluoromethylcyclohexyl) ethyl group, 3-(2,2-difluorocyclopropyl) propyl group, 4-(2,2-difluorocyclopropyl) butyl group, and the like, but are not limited thereto.

Examples of "the C3 to C6 cycloalkyl C1 to C6 alkyl group, wherein the C3 to C6 cycloalkyl group moiety may be monosubstituted or polysubstituted by a halogen atom or a C1 to C4 alkyl group" include, but are not limited to, the appropriate examples of the above examples.

The phenyl C1 to C6 alkyl group means a C1 to C6 alkyl group substituted by phenyl (wherein the C1 to C6 alkyl group moiety has the same meaning as defined above).

Examples of phenyl C1 to C6 alkyl groups include, but are not limited to, benzyl group, 1-phenylethyl group, 2-phenylethyl group, 3-phenylpropyl group, 4-phenylbutyl group, 5-phenylpentyl group, 6-phenylhexyl and the like.

Examples of "phenyl C1 to C6 alkyl group, wherein the phenyl group moiety may be monosubstituted or polysubstituted by halogen atom, C1 to C4 alkyl group, C1 to C4 alkoxy group, C1 to C6 haloalkyl group, cyano group or nitro group" include, but are not limited to, the examples of the above phenyl C1 to C6 alkyl groups, and 2-(4-fluorophenyl) ethyl, 2-(3,4,5-trifluorophenyl)ethyl group, 2-(4-methylphenyl)ethyl group, 2-(4-methoxyphenyl)ethyl group, 2-(4-trifluoromethylphenyl)ethyl group, 2-(4-cyanophenyl) ethyl group, 2-(4-nitrophenyl) ethyl group, 3-(4-fluorophenyl) propyl group, 4-(4-fluorophenyl) butyl group, 5-(4-fluorophenyl) pentyl group, and the like.

Examples of "a phenyl C1 to C6 alkyl group, wherein the phenyl group moiety may be monosubstituted or polysubstituted by a halogen atom or a C1 to C4 alkyl group" include, but are not limited to, the appropriate examples of the above examples.

C3 to C6 cycloalkyl C1 to C6 haloalkyl group means a C1 to C6 haloalkyl group substituted by a C3 to C6 cycloalkyl group (wherein the C3 to C6 cycloalkyl group moiety and the C1 to C6 haloalkyl group moiety have the same meaning as defined above).

Examples of C3 to C6 cycloalkyl C1 to C6 haloalkyl groups include, but are not limited to, a 2-cyclopropyl-2,2-difluoroethyl group, a 3-cyclopropyl-3,3-difluoropropyl group, a 4-cyclopropyl-4,4-difluorobutyl group, a 5-cyclopropyl-5,5-difluoropentyl group, a 6-cyclopropyl-6,6-difluorohexyl group, a 2-cyclobutyl-2,2-difluoroethyl group, a 2-cyclopentyl-2,2-difluoroethyl group, a 2-cyclohexyl-2,2-difluoroethyl group and the like.

Examples of "C3 to C6 cycloalkyl C1 to C6 haloalkyl group wherein the C3 to C6 cycloalkyl group moiety may be monosubstituted or polysubstituted by a halogen atom, a C1 to C4 alkyl group, a C1 to C4 alkoxy group, a C1 to C4 haloalkyl group" include, but are not limited to, examples of the above C3 to C6 cycloalkyl C1 to C6 haloalkyl groups and examples of a 2-(2,2-difluorocyclopropyl)-2,2-difluoroethyl group, a 2-(4,4-difluorocyclohexyl)-2,2-difluoroethyl group, 2-(4-tert-butylcyclohexyl) -2,2-difluoroethyl group, 2-(4-methoxycyclohexyl)-2,2-difluoroethyl group, 2-(4-trifluoromethylcyclohexyl)-2,2-difluoroethyl group, 3-(2,2-difluorocyclopropyl) -3,3-difluoropropyl group, 4-(2,2-difluorocyclopropyl) -4,4-difluorobutyl group and the like.

Examples of "a C3 to C6 cycloalkyl C1 to C6 haloalkyl group whewein the C3 to C6 cycloalkyl group moiety may be monosubstituted or polysubstituted by a halogen atom or a C1 to C4 alkyl group" include, but are not limited to, the appropriate examples of the above examples.

The phenyl C1 to C6 haloalkyl group means a C1 to C6 haloalkyl group substituted by phenyl (wherein the C1 to C6 haloalkyl group moiety has the same meaning as defined above).

Examples of phenyl C1 to C6 haloalkyl groups include, but are not limited to, 2-phenyl-2,2-difluoroethyl group, 3-phenyl-3,3 -difluoropropyl group, 4-phenyl-4,4-difluorobutyl group, 5-phenyl-5,5-difluoropentyl group and the like.

Examples of "Phenyl C1 to C6 haloalkyl group, wherein the phenyl group moiety may be monosubstituted or polysubstituted by a halogen atom, a C1-C4 alkyl group, a C1-C4 alkoxy group, a C1-C6 haloalkyl group, a cyano group or a nitro group" include, but are not limited to, the examples of the above phenyl C1 to C6 haloalkyl group and examples of 2-(4-fluorophenyl)-2,2-difluoroethyl group, 2-(3,4,5-trifluorophenyl) -2,2-difluoroethyl group, 2-(4-methylphenyl)-2,2-difluoroethyl group, 2-(4-methoxyphenyl)-2,2-difluoroethyl group, 2-(4-trifluoromethylphenyl)-2,2-difluoroethyl group, 2-(4-cyanophenyl) -2,2-difluoroethyl group, 2-(4-nitrophenyl)-2,2-difluoroethyl group, 3-(4-fluorophenyl) -3,3 -difluoropropyl group, 4-(4-fluorophenyl)-4,4-difluorobutyl group, 5-(4-fluorophenyl)-5,5-difluoropentyl group and the like.

Examples of "a phenyl C1 to C6 haloalkyl group, wherein the phenyl group moiety may be monosubstituted or polysubstituted by a halogen atom or a C1 to C4 alkyl group" include, but are not limited to, appropriate examples of the above examples.

C1 to C4 alkoxy C2 to C10 alkyl group means a C2 to C10 alkyl group substituted by C1 to C4 alkoxy group (wherein the C1 to C4 alkoxy group and the C2 to C10 alkyl group have the same meaning as described above).

Examples of C1 to C4 alkoxy C2 to C10 alkyl groups include, but are not limited to, 5-methoxypentyl group, 6-methoxyhexyl group and the like.

C1 to C4 haloalkoxy C2 to C10 alkyl group means a C2 to C10 alkyl group substituted by C1 to C4 haloalkoxy group (wherein the C1 to C4 haloalkoxy group and the C2-C10 alkyl group have the same meaning as described above).

Examples of C1 to C4 haloalkoxy C2 to C10 alkyl groups include, but are not limited to, 5-difluoromethoxypentyl group, 5-trifluoromethoxypentyl group, 6-difluoromethoxyhexyl group, 6-trifluoromethoxyhexyl group and the like.

C1 to C4 alkylthio C2 to C10 alkyl group means a C2 to C10 alkyl group substituted by C1 to C4 alkylthio group (wherein the C1 to C4 alkylthio group and the C2 to C10 alkyl group have the same meaning as described above).

Examples of C1 to C4 alkylthio C2 to C10 alkyl groups include, but are not limited to, 2-methylthioethyl group, 3-methylthiopropyl group, 4-methylthiobutyl group, 5-methylthiopentyl group, 5-ethylthiopentyl group, 5-propylthiopentyl group, 5-butylthiopentyl group, 6-methylthiohexyl group, 6-ethylthiohexyl group, 6-propylthiohexyl group, 6-butylthiohexyl group, 7-methylthioheptyl group, 8-methylthiooctyl group, 9-methylthiononyl group, 10-methylthiodecyl group and the like.

From the viewpoints of the usefulness and economy of the product etc., preferable examples of the C1 to C4 alkylthio C2 to C10 alkyl group include a 5-methylthiopentyl group and a 6-methylthiohexyl group.

C1 to C4 haloalkylthio C2 to C10 alkyl group means a C2 to C10 alkyl group substituted by C1 to C4 haloalkylthio group (wherein the C1 to C4 haloalkylthio group and the C2 to C10 alkyl group have the same meaning as described above).

Examples of C1 to C4 haloalkylthio C2 to C10 alkyl group include, but are not limited to, 2-trifluoromethylthioethyl group, 3-trifluoromethylthiopropyl group, 4-trifluoromethylthiobutyl group, 5-difluoromethylthiopentyl group, 5-trifluoromethylthiopentyl group, 5-(2,2,2-trifluoroethylthio)pentyl group, 5-pentafluoroethylthiopentyl group, 5-(2,2,3,3,3-pentafluoropropylthio)pentyl group, 5-(2,2,3,3,4,4,4-heptafluorobutylthio)pentyl group, 6-difluoromethylthiohexyl group, 6-trifluoromethylthiohexyl group, a 6-(2,2,2-trifluoroethylthio)hexyl group, 6-pentafluoroethylthiohexyl group, 6-(2,2,3,3,3-pentafluoropropylthio) hexyl group, 6-(2,2,3,3,4,4,4-heptafluorobutylthio)hexyl group, 7-trifluoromethylthioheptyl group, 8-trifluoromethylthiooctyl group, 9-trifluoromethylthi ononyl group, 10-trifluoromethylthiododecyl group and the like.

Preferred examples of the C1 to C4 haloalkylthio C2 to C10 alkyl group include a 5-trifluoromethylthiopentyl group and a 6-trifluoromethylthiohexyl group from the viewpoints of product usefulness and economic efficiency and the like.

C1 to C4 alkylsulfinyl C2 to C10 alkyl group means a C2 to C10 alkyl group substituted by C1 to C4 alkylsulfinyl group (wherein the C1 to C4 alkylsulfinyl group and the C2 to C10 alkyl group have the same meaning as described above).

Examples of C1 to C4 alkylsulfinyl C2 to C10 alkyl groups include, but are not limited to, 5-methylsulfinylpentyl group and 6-methylsulfinylhexyl group, and the like.

C1 to C4 alkylsulfonyl C2 to C10 alkyl group means a C2 to C10 alkyl group substituted by C1 to C4 alkylsulfonyl group (wherein the C1 to C4 alkylsulfonyl group and the C2 to C10 alkyl group have the same meanings as described above).

Examples of C1 to C4 alkylsulfonyl C2 to C10 alkyl groups include, but are not limited to, 5-methylsulfonylpentyl group and 6-methylsulfonylhexyl group and the like.

C1 to C4 haloalkylsulfinyl C2 to C10 alkyl group means a C2 to C10 alkyl group substituted by C1 to C4 haloalkylsulfinyl group (wherein the C1 to C4 haloalkylsulfinyl group and the C2 to C10 alkyl group have the same meanings as described above).

Examples of the C1 to C4 haloalkylsulfinyl C2 to C10 alkyl group include, but are not limited to, 5-difluoromethylsulfinylpentyl group, 5-trifluoromethylsulfinyl pentyl group, 6-difluoromethylsulfinylhexyl group, 6-trifluoromethylsulfinylhexyl group and the like.

C1 to C4 haloalkylsulfonyl C2 to C10 alkyl group means a C2 to C10 alkyl group substituted by C1 to C4 haloalkylsulfonyl group (wherein the C1 to C4 haloalkylsulfonyl group and the C2 to C10 alkyl group have the same meanings as described above).

Examples of C1 to C4 haloalkylsulfonyl C2 to C10 alkyl groups include, but are not limited to, 5-difluoromethylsulfonylpentyl group, 5-trifluoromethylsulfonylpentyl group, 6-difluoromethylsulfonylhexyl group, 6-trifluoromethylsulfonylhexyl group and the like.

C6 to C10 aryl group means an aromatic cyclic group in which all the atoms constituting the ring are 6 to 10 carbon atoms.

Examples of C6 to C10 aryl groups are phenyl, 1-naphthyl, and 2-naphthyl. 1-Naphthyl group is also referred to as a naphthalen-1-yl group. 2-Naphthyl group is also referred to as a naphthalene-2-yl group.

C1 to C4 alkoxycarbonyl group means a (C1 to C4 alkyl)—O—C (=O)— group (wherein the C1 to C4 alkyl group moiety has the same meaning as defined above).

Examples of C1 to C4 alkoxycarbonyl groups include, but are not limited to, methoxycarbonyl group, ethoxycarbonyl group, propoxycarbonyl group, isopropoxycarbonyl group, butoxycarbonyl group and the like.

C1 to C4 alkylcarbonyl group means a (C1 to C4 alkyl)—C(=O)— group (wherein the C1 to C4 alkyl group moiety has the same meaning as defined above).

Examples of C1 to C4 alkylcarbonyl groups include, but are not limited to, acetyl group, propionyl group, butyryl group, isobutyryl group, valeryl group and the like.

The hydroxy C1 to C4 alkyl group means a C1 to C4 alkyl group substituted with a hydroxy group (wherein the C1 to C4 alkyl group has the same meaning as described above).

Examples of hydroxy C1 to C4 alkyl groups include, but are not limited to, hydroxymethyl group, 1-hydroxyethyl group, 2-hydroxyethyl group, 1-hydroxypropyl group, 2-hydroxypropyl group, 1-hydroxybutyl group, 2-hydroxybutyl group, 3-hydroxybutyl group and the like.

C1 to C4 alkoxy C1 to C4 alkyl group means a C1 to C4 alkyl group substituted by a C1 to C4 alkoxy group (wherein the C1 to C4 alkoxy group and the C1 to C4 alkyl group have the same meaning as described above).

Examples of C1 to C4 alkoxy C1 to C4 alkyl groups include, but are not limited to, methoxyethyl group, ethoxymethyl group, propoxymethyl group, isopropoxymethyl group, 1-methoxyethyl group,2-methoxyethyl group, 1-ethoxyethyl group, 2-ethoxyethyl group, 1-propoxyethyl group, 2-propoxy ethyl group, 1-isopropoxyethyl group, 2-isopropoxyethyl group, 1-methoxypropyl group, 2-methoxypropyl group, 3-methoxypropyl group, 1-methoxybutyl group, 2-methoxybutyl group, 3-methoxybutyl group, 4-methoxybutyl group and the like.

The amino C1 to C4 alkyl group means a C1 to C4 alkyl group substituted by an amino group (wherein the C1 to C4 alkyl group has the same meaning as described above).

Examples of amino C1 to C4 alkyl groups include, but are not limited to, aminomethyl group, 1-aminoethyl group, 2-aminoethyl group, 1-aminopropyl group, 2-aminopropyl group, 1-aminobutyl group, 2-aminobutyl group, 3-aminobutyl group and the like.

The cyano C1 to C4 alkyl group means a C1 to C4 alkyl group substituted by a cyano group (wherein the C1 to C4 alkyl group has the same meaning as described above).

Examples of cyano C1 to C4 alkyl groups include, but are not limited to, cyanomethyl group, 1-cyanoethyl group, 2-cyanoethyl group, 1-cyanopropyl group, 2-cyanopropyl group, 1-cyanobutyl group, 2-cyanobutyl group, 3-cyanobutyl group and the like.

The nitro C1 to C4 alkyl group means a C1 to C4 alkyl group substituted by a nitro group (wherein the C1 to C4 alkyl group has the same meaning as described above).

Examples of nitro C1 to C4 alkyl groups include, but are not limited to, nitromethyl group, 1-nitroethyl group, 2-nitroethyl group, 1-nitropropyl group, 2-nitropropyl group, 1-nitrobutyl group, 2-nitrobutyl group, 3-nitrobutyl group and the like.

The carboxy C1 to C4 alkyl group means a C1 to C4 alkyl group substituted by a carboxy group (wherein the C1 to C4 alkyl group has the same meaning as described above).

Examples of carboxy C1 to C4 alkyl groups include, but are not limited to, carboxymethyl group, 1-carboxyethyl group, 2-carboxyethyl group, 1-carboxypropyl group, 2-carboxypropyl group, 1-carboxybutyl group, 2-carboxybutyl group, 3-carboxybutyl group and the like.

C1 to C4 alkoxycarbonyl C1 to C4 alkyl group means a C1 to C4 alkyl group substituted by C1 to C4 alkoxycarbonyl group (wherein the C1 to C4 alkoxycarbonyl group and the C1 to C4 alkyl group have the same meaning as described above).

Examples of C1 to C4 alkoxycarbonyl C1 to C4 alkyl groups include, but are not limited to, a methoxycarbonylmethyl group, an ethoxycarbonylmethyl group, a propoxycarbonylmethyl group, an isopropoxycarbonylmethyl group, a 1-methoxycarbonylethyl group, a 2-methoxycarbonylethyl group, a 1-ethoxycarbonylethyl group, a 2-ethoxycarbonylethyl group, a 1-propoxycarbonylethyl group, a 2-propoxycarbonylethyl group, a 1-isopropoxycarbonylethyl group, a 2-isopropoxycarbonylethyl group, a 1-methoxycarbonylpropyl group, a 2-methoxycarbonylpropyl group, a 3-methoxycarbonylpropyl group, a 1-methoxycarbonylbutyl group, a 2-methoxycarbonylbutyl group, a 3-methoxycarbonylbutyl group, a 4-methoxycarbonylbutyl group and the like.

The mono (C1 to C4 alkyl) amino group means a (C1 to C4 alkyl)—NH— group (wherein the C1 to C4 alkyl group moiety has the same meaning as defined above).

Examples of mono (C1 to C4 alkyl) amino group include, but are not limited to, methylamino group, ethylamino group, propylamino group, isopropylamino group, butylamino group and the like.

The di(C1 to C4 alkyl) amino group means a (C1 to C4 alkyl)$_2$N— group (wherein the C1 to C4 alkyl group moieties are the same or different and have the same meaning as defined above).

Examples of the di (C1 to C4 alkyl) amino group include, but are not limited to, a dimethylamino group, a diethylamino group, a dipropylamino group, a dibutylamino group, a methylethylamino group and the like.

Definitions and examples of functional groups other than those described above can be understood by those skilled in the art as well as the above functional groups.

(Starting Compound: Sulfide Derivative Represented by General Formula (2))

The preparation of the sulfide derivative represented by the general formula (2) will be described, for example, in International Publication No. 2013/157229 (Patent Document 1) or in a similar manner.

From the viewpoints of the usefulness and economy of the product etc., preferred combinations of $R^1$, $R^2$ and $R^3$ in the general formula (2) are:

$R^1$ is a C1 to C10 alkyl group, a C3 to C6 cycloalkyl C1 to C6 alkyl group, wherein the said C3 to C6 cycloalkyl group moiety may be monosubstituted or polysubstituted by halogen atoms or C1 to C4 alkyl groups, a phenyl C1 to C6 alkyl group, wherein the said phenyl group moiety may be monosubstituted or polysubstituted by halogen atoms or C1 to C4 alkyl groups, a C1 to C4 alkoxy C2 to C10 alkyl group, a C1 to C4 haloalkoxy C2 to C10 alkyl group, a C1 to C4 alkylthio C2 to C10 alkyl group, a C1 to C4 alkylsulfinyl C2 to C10 alkyl group, a C1 to C4 alkyl sulfonyl C2 to C10 alkyl group, a C1 to C4 haloalkylthio C2 to C10 alkyl group, a C1 to C4 haloalkylsulfinyl C2 to C10 alkyl group, a C1 to C4 haloalkylsulfonyl C2 to C10 alkyl group,
a C1 to C6 haloalkyl group,
a C3 to C6 cycloalkyl C1 to C6 haloalkyl group wherein the said C3 to C6 cycloalkyl group moiety may be monosubstituted or polysubstituted by halogen atoms or C1 to C4 alkyl groups,
a phenyl C1 to C6 haloalkyl group wherein the phenyl group moiety may be monosubstituted or polysubstituted by a halogen atom or a C1 to C4 alkyl group;
$R^2$ and $R^3$ are each independently a halogen atom or a C1 to C4 alkyl group.

From the same viewpoint as above, in the general formula (2), more preferable combinations of $R^1$, $R^2$ and $R^3$ are:
$R^1$ is a C1 to C10 alkyl group,
a C1 to C4 alkoxy C2 to C10 alkyl group,
a C1 to C4 haloalkoxy C2 to C10 alkyl group,
a C1 to C4 alkylthio C2 to C10 alkyl group,
a C1 to C4 alkylsulfinyl C2 to C10 alkyl group,
a C1 to C4 alkyl sulfonyl C2 to C10 alkyl group,
a C1 to C4 haloalkylthio C2 to C10 alkyl group,
a C1 to C4 haloalkylsulfinyl C2 to C10 alkyl group,
a C1 to C4 haloalkylsulfonyl C2 to C10 alkyl group, or
a C1 to C6 haloalkyl group; and
$R^2$ and $R^3$ are each independently a halogen atom or a C1 to C4 alkyl group.

From the same viewpoint as above, a further preferable combination of $R^1$, $R^2$ and $R^3$ in the general formula (2) is:
$R^1$ is a C1 to C4 haloalkylthio C2 to C10 alkyl group; and
$R^2$ and $R^3$ are each independently a halogen atom or a C1 to C4 alkyl group.

From the same viewpoint as above, a further preferable combination of $R^1$, $R^2$ and $R^3$ in the general formula (2) is:
$R^1$ is a 5-trifluoromethylthiopentyl group or a 6-trifluoromethylthiohexyl group; and either $R^2$ is a fluorine atom and $R^3$ is a chlorine atom, or $R^2$ and $R^3$ are methyl groups.

In one embodiment, from the same viewpoint as above, a further preferable specific combination of $R^1$, $R^2$ and $R^3$ in the general formula (2) is:
$R^1$ is a 5-trifluoromethylthiopentyl group;
$R^2$ is a fluorine atom; and
$R^3$ is a chlorine atom.

In another embodiment, from the same viewpoint as above, a further preferable specific combination of $R^1$, $R^2$ and $R^3$ in the general formula (2) is:
$R^1$ is a 6-trifluoromethylthiohexyl group; and
$R^2$ and $R^3$ are methyl groups.

From the same viewpoint as above, particularly preferred specific combinations of $R^1$, $R^2$ and $R^3$ in the general formula (2) are:
$R^1$ is a 5-trifluoromethylthiopentyl group;
$R^2$ is a fluorine atom; and
$R^3$ is a chlorine atom.

(Titled Compound: Sulfoxide Derivative Represented by the General Formula (1))

From the same viewpoint as described above, preferable combinations, more preferable combinations, further more preferable combinations, and particularly preferable combinations of $R^1$, $R^2$ and $R^3$ in the general formula (1) are the same as those in the general formula (2).

(Oxidizing Agent)

The oxidizing agent used in the present invention may be any oxidizing agent as long as the reaction proceeds. Any oxidizing agent capable of oxidizing the corresponding starting compound (sulfide derivative) to titled compound (sulfoxide derivative) can be used. Examples of the oxidizing agent used in the present invention include, but are not limited to, inorganic peroxides (such as hydrogen peroxide, urea-hydrogen peroxide adducts, etc.) and the like. From the viewpoints of safety, reactivity, selectivity, economic efficiency and the like. The preferred oxidizing agent is hydrogen peroxide. The oxidizing agent may be used alone or in combination of two or more in any proportion.

The form of the oxidizing agent may be in any form as long as the reaction proceeds. The form of the oxidizing agent can be appropriately selected by those skilled in the art. When hydrogen peroxide is used as the oxidizing agent, the form of hydrogen peroxide may be in any form as long as the reaction proceeds. Considering the danger and economic efficiency, an example of hydrogen peroxide in a preferred form is a 5 to 60 wt % aqueous hydrogen peroxide solution, more preferably a 5 to 40 wt % hydrogen peroxide aqueous solution, further more preferably a 10 to 35 wt % hydrogen peroxide aqueous solution, in particular preferably 25 to 35 wt % hydrogen peroxide aqueous solution. In this specification, for example, "30% hydrogen peroxide aqueous solution" is also referred to as "30% hydrogen peroxide".

(Amount of Oxidizing Agent Used)

The amount of the oxidizing agent used in the method of the present invention may be any amount as long as the reaction proceeds.

From the viewpoint of improving the yield and economic efficiency, etc., the low limit of the oxidizing agent in the present invention, can be exemplified by 0.9 mol or more, preferably 1.0 mol or more, based on 1 mol of the sulfide derivative (starting compound) represented by the general formula (2).

From the viewpoints of safety, suppression of byproducts, economic efficiency, etc., the upper limit of the oxidizing agent in the present invention, can be exemplified by 4.0 moles or less, preferably 3.0 moles or less, and more preferably 2.5 moles or less, based on 1 mole of the sulfide derivative represented by the general formula (2)(starting compound).

Further, as an amount of the oxidizing agent to be used in the present invention, an appropriate and any combination of the above lower limit and the above upper limit can be exemplified. Therefore, from the viewpoints of safety, improvement of yield, suppression of byproducts, economic efficiency, etc., the amount of the oxidizing agent used in the present invention, can be exemplified by 0.9 to 4.0 moles, preferably 1.0 to 3.0 moles, and more preferably 1.0 to 2.5 moles based on 1 mole of the sulfide derivative (starting compound) represented by the general formula (2). However, the amount of the oxidizing agent used in the present invention can be appropriately adjusted by those skilled in the art depending on the purpose and situation.

(Catalyst: Metal-ligand Complex)

The catalyst in the present invention is a metal-ligand complex. Metal-ligand complexes can be prepared from metal compounds and ligands. In addition, the metal-ligand complex may contain components other than the metal compound and the ligand. Thus, the metal-ligand complex comprises a metal compound ligand.

(Metal Compound)

The metal compound contained in the metal-ligand complex in the present invention will be described. The metal compound used in the present invention may be any metal compound as long as the reaction proceeds. The metal compound used in the present invention is a known compound or a compound that can be produced from known compounds according to known methods.

The metal compound includes, but is not limited to, metal acetylacetonate, a metal halide, a metal oxide, a metal alkoxide and the like.

The metal of the metal compound is preferably a transition metal.

Examples of the metal compound include, but are not limited to, an iron compound, a vanadium compound, a titanium compound, a manganese compound, a copper compound, a molybdenum compound, a zirconium compound, and the like.

From the viewpoint of yield, economic efficiency, etc., the metal compound is preferably an iron compound, a vanadium compound, more preferably an iron compound.

Examples of iron compounds include, but are not limited to, iron (III) acetylacetonate, iron (III) chloride, iron (III) bromide, iron (III) methoxide, iron (III) ethoxide, iron (III) propoxide, iron(III) Isopropoxide, and the like. "Iron (III) acetylacetonate" is also referred to as "Fe(acac)$_3$" or "tris (2,4-pentanedionato) iron (III)". Preferred examples of the iron compound include iron (III) acetylacetonate, iron (III) chloride from the same viewpoint as described above. A more preferable example of the iron compound includes iron (III) acetylacetonate.

Examples of vanadium compounds include, but are not limited to, vanadyl acetylacetonate, vanadium oxide (V), triisopropoxy vanadium (V) oxide, and the like. "Vanadyl acetylacetonate" is also referred to as "VO(acac)$_2$", "bis (2,4-pentanedionato) vanadium (IV) oxide" or "vanadium (IV) oxyacetylacetonate". "Triisopropoxy vanadium (V) oxide" is also referred to as "VO(OiPr)$_3$" or "triisopropoxyoxovanadium (V)". From the same viewpoint as above, preferred examples of the vanadium compound include vanadyl acetylacetonate and vanadium oxide (V). A more preferable example of a vanadium compound includes vanadyl acetylacetonate.

Examples of titanium compounds include, but are not limited to, titanium tetrachloride, titanium (IV) methoxide, titanium (IV) ethoxide, titanium (IV) propoxide, titanium (IV) isopropoxide, titanium (IV) tert-butoxide and the like.

Examples of manganese compounds include, but are not limited to, manganese (III) acetylacetonate, manganese (II) chloride, and the like. "Manganese (III) acetylacetonate" is also called "Mn(acac)$_3$".

Examples of copper compounds include, but are not limited to, copper (II) acetylacetonate, copper (I) chloride, copper (II) chloride and the like. "copper (II) acetylacetonate" is also referred to as "Cu(acac)$_2$".

Examples of molybdenum compounds include, but are not limited to, molybdenyl acetylacetonate, and the like. "Molybdenyl acetylacetonate" is also referred to as "MoO$_2$(acac)$_2$", "bis(2,4-pentanedionato) molybdenum (VI) dioxide" or "molybdenum (IV) dioxyacetylacetonate".

Examples of zirconium compounds include, but are not limited to, zirconium (IV) acetylacetonate, zirconium tetrachloride and the like. "Zirconium (IV) acetylacetonate" is also referred to as "Zr(acac)$_4$" or "tetrakis (2,4-pentanedionato) zirconium (IV)".

The metal compounds in the present invention may be used alone or in combination of two or more in any ratio. The form of the metal compound in the present invention may be in any form as long as the reaction proceeds. The form of the metal compound in the present invention can be appropriately selected by those skilled in the art.

(Amount of Metal Compound Used)

The amount of the metal compound used in the method of the present invention may be in any amount as long as the reaction proceeds. The amount of the metal compound used can be reduced by using the benzoic acid compound represented by the general formula (4). In one embodiment, from the viewpoint of improving the yield, reducing the environmental burden, economic efficiency, etc., the amount of the metal compound used in the present invention is, 0.1 to 20.0 mol %, preferably 0.1 to 10.0 mol %, more preferably 0.3 to 10 mol %, in particular preferably 0.4 to 10.0 mol %., based on 1 mol of the sulfide derivative (starting compound) represented by the general formula (2). Furthermore, in another embodiment, from the same viewpoint as described above, the amount of the metal compound used in the present invention is, preferably 0.3 to 6.0 mol %, more preferably 0.3 to 5.0 mol %, more preferably 0.4 to 5.0 mol %, more preferably 0.4 to 4.0 mol %, further more preferably 0.4 to 3.0 mol % and particularly preferably 0.4 to 2.0 mol %, based on 1 mol of the sulfide derivative (starting compound) represented by the general formula (2). However, the amount of the metal compound used in the present invention can be appropriately adjusted by those skilled in the art depending on the purpose and the situation.

(Ligand)

The ligand contained in the metal-ligand complex in the present invention will be described. The ligand used in the present invention is a known compound or a compound that can be produced from known compounds according to known methods.

From the viewpoint of yield, economic efficiency, etc., preferred ligands are represented by the general formula (3):

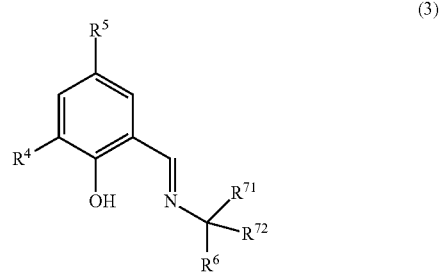

(wherein, $R^4$, $R^5$, $R^6$, $R^{71}$ and $R^{72}$ are as defined below).

In the general formula (3), $R^4$ and $R^5$ are each independently a hydrogen atom, a halogen atom, a C1 to C6 alkyl group, a phenyl C1 to C6 alkyl group, a C6 to C10 aryl group, a cyano group, a nitro group or a C1 to C6 alkoxy group.

From the viewpoints of yield, economic efficiency and the like, preferred examples of $R^4$ and $R^5$ are each independently a hydrogen atom, a halogen atom or a C1 to C6 alkyl group, more preferably each independently a hydrogen atom or a halogen atom.

A more preferable example of $R^4$ is a hydrogen atom.

More preferred examples of $R^5$ are a hydrogen atom or a chlorine atom, particularly preferably a hydrogen atom.

In the general formula (3), $R^6$ is a C1 to C4 alkyl group, a cyano group, a nitro group, a carboxy group, a C1 to C4 alkoxycarbonyl group, a C1 to C4 alkylcarbonyl group, a hydroxy C1 to C4 alkyl group, a C1 to C4 alkoxy C1 to C4 alkyl group, an amino C1 to C4 alkyl group, a cyano C1 to C4 alkyl group, a nitro C1 to C4 alkyl group, a carboxy C1 to C4 alkyl group or a C1 to C4 alkoxy carbonyl C1 to C4 alkyl group.

From the viewpoints of yield, economic efficiency and the like, preferable examples of $R^6$ are hydroxy C1 to C4 alkyl groups, more preferably hydroxymethyl groups.

In the general formula (3), $R^{71}$ and $R^{72}$ are each independently a hydrogen atom, a C1 to C6 alkyl group, a phenyl C1 to C6 alkyl group or a C6 to C10 aryl group, provided that the case where both of $R^{71}$ and $R^{72}$ are hydrogen atoms is excluded.

From the viewpoint of yield and economic efficiency, etc., preferred examples of $R^{71}$ and $R^{72}$ are each independently a hydrogen atom or a C1 to C6 alkyl group, provided that the case where both $R^{71}$ and $R^{72}$ are hydrogen atoms is excluded, more preferably, either $R^{71}$ is a methyl group and $R^{72}$ is a methyl group, or $R^{71}$ is a hydrogen atom and $R^{72}$ is an isopropyl group, particularly preferably $R^{71}$ is a methyl group and $R^{72}$ is a methyl group.

In the general formula (3), preferable specific combinations of $R^4$, $R^5$, $R^6$, $R^{71}$ and $R^{72}$ are as follows:

$R^4$ is a hydrogen atom;

$R^5$ is a hydrogen atom or a chlorine atom;

$R^6$ is a hydroxymethyl group;

$R^{71}$ is a methyl group;

$R^{72}$ is a methyl group.

Particularly preferred specific combinations of $R^4$, $R^5$, $R^6$, $R^{71}$ and $R^{72}$ in the general formula (3) are:

$R^4$ is a hydrogen atom;

$R^5$ is a hydrogen atom;

$R^6$ is a hydroxymethyl group;

$R^{71}$ is a methyl group;

$R^{72}$ is a methyl group.

Specific examples of the ligand, the related ligand, and other ligands used in the examples and comparative examples of the present invention are shown below.

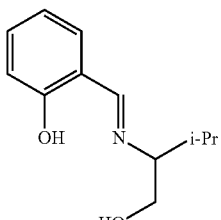

(3-1)

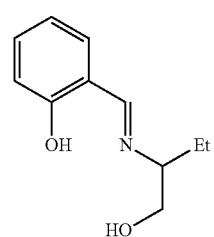

(3-2)

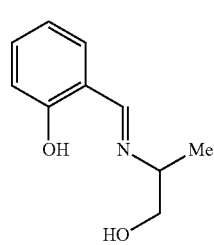

(3-3)

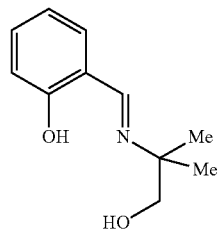

(3-4)

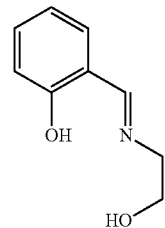

(3-5)

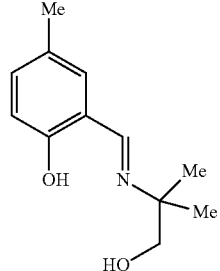

(3-6)

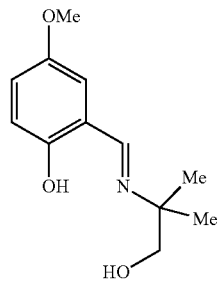

(3-7)

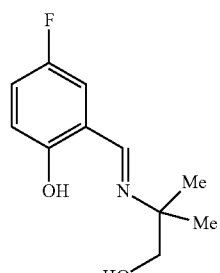

(3-8)

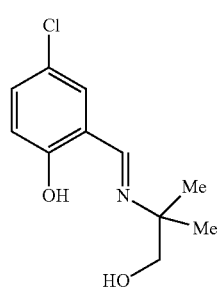

(3-9)

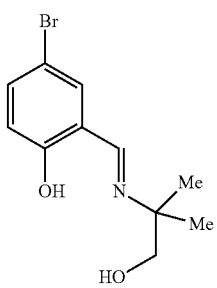
(3-10)

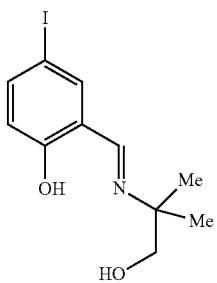
(3-11)

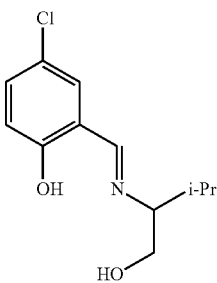
(3-12)

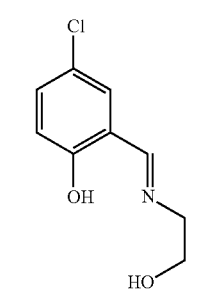
(3-13)

From the viewpoints of yield, economic efficiency and the like, preferable examples of the ligand include the formula (3-1), (3-2), (3-3), (3-4), (3-8) (3-9), (3-10), and (3-12).

More preferred specific examples of the ligand include the formulas (3-1), (3-2), (3-3), (3-4), (3-9), or (3-12).

More preferred specific examples of the ligand are the formula (3-1), (3-4), (3-9), or (3-12).

Further preferred examples of the ligand are the formula (3-4) or (3-9).

A particularly preferred embodiment of the ligand is a compound of formula (3-4).

The ligand in the present invention may be used alone or in combination of two or more in any proportion. The form of the ligand in the present invention may be in any form as long as the reaction proceeds. The form of the ligand compound in the present invention can be appropriately selected by those skilled in the art.

(Amount of Ligand Used)

The amount of the ligand used in the method of the present invention may be any amount as long as the reaction proceeds. The use amount of the ligand can be reduced by using the benzoic acid compound represented by the general formula (4). In one embodiment, from the viewpoints of improvement of yield, reduction of environmental burden, economic efficiency, etc., the amount of the ligand used in the present invention is, 0.1 to 20.0 mol %, preferably 0.1 to 10.0 mol %, more preferably 0.3 to 10.0 mol %, and particularly preferably 0.4 to 10.0 mol %, based on 1 mol of the sulfide derivative (starting compound) represented by the general formula (2). Furthermore, in another embodiment, from the same viewpoint as above, the amount of the ligand used in the present invention is, preferably 0.3 to 6.0 mol %, more preferably 0.3 to 5.0 mol %, still more preferably 0.4 to 5.0 mol %, still preferably 0.4 to 4.0 mol %, still more preferably 0.4 to 3.0 mol %, particularly preferably 0.4 to 2.0 mol %, based on 1 mol of the sulfide derivative (starting compound) represented by the general formula (2). However, the amount of the ligand used in the present invention can be appropriately adjusted by those skilled in the art depending on the purpose and the situation.

(Benzoic Acid Compound)

The benzoic acid compound represented by the general formula (4) in the present invention will be described. The reaction of the present invention is carried out in the presence of a benzoic acid compound represented by the general formula (4):

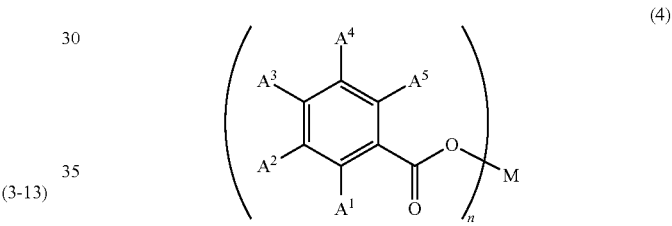
(4)

(wherein, $A^1$, $A^2$, $A^3$, $A^4$, $A^5$, M and n are as defined below). The benzoic acid compound of the general formula (4) used in the present invention is a known compound or a compound which can be produced according to a known method from known compounds.

From the viewpoints of yield, economic efficiency, etc., the preferable examples of $A^1$, $A^2$, $A^3$, $A^4$ and $A^5$ in the general formula (4), are $A^1$ is a C1 to C2 alkoxy group;
$A^2$ is a hydrogen atom;
$A^3$ is a hydrogen atom or a C1 to C2 alkoxy group;
$A^4$ is a hydrogen atom;
$A^5$ is a C1 to C2 alkoxy group.

A more preferable example of $A^1$ is a methoxy group.

More preferable examples of $A^3$ are a hydrogen atom or a methoxy group, and more preferably a hydrogen atom.

A more preferable example of $A^5$ is a methoxy group.

In the general formula (4), M is a hydrogen atom, an alkali metal atom or an alkaline earth metal atom.

From the viewpoints of yield and economic efficiency, etc., M is preferably an alkali metal atom or an alkaline earth metal atom, more preferably an alkali metal atom.

Specific examples of M include, but are not limited to, lithium atom, sodium atom, potassium atom, cesium atom, magnesium atom, calcium atom, and barium atom.

Preferred specific examples of M are lithium atom, sodium atom, potassium atom, cesium atom, magnesium atom, and calcium atom from the viewpoints of yield, economic efficiency, and the like.

More preferred examples of M are a lithium atom, a sodium atom, a potassium atom, and a cesium atom.

A further preferred example of M is a sodium atom.

In the general formula (4), n is 1 or 2. More specifically, as long as it is chemically acceptable, n may be 1 or 2. For example, when M is a hydrogen atom or an alkali metal atom, n is 1. As another example, when M is an alkaline earth metal atom, n is 2.

From the viewpoints of yield, economic efficiency, etc., preferred combinations of $A^1, A^2, A^3, A^4, A^5$, M and n in the general formula (4) are:
$A^1$ is a C1 to C2 alkoxy group;
$A^2$ is a hydrogen atom;
$A^3$ is a hydrogen atom or a C1 to C2 alkoxy group;
$A^4$ is a hydrogen atom;
$A^5$ is a C1 to C2 alkoxy group;
M is a sodium atom; and
n is 1.

More preferred combinations of $A^1, A^2, A^3, A^4, A^5$, M and n in the general formula (4) are:
$A^1$ is a methoxy group;
$A^2$ is a hydrogen atom;
$A^3$ is a hydrogen atom or a methoxy group;
$A^4$ is a hydrogen atom;
$A^5$ is a methoxy group;
M is a sodium atom; and
n is 1.

In one embodiment in a further preferred specific combination of $A^1, A^2, A^3, A^4, A^5$, M and n in the general formula (4) are:
$A^1$ is a methoxy group;
$A^2$ is a hydrogen atom;
$A^3$ is a hydrogen atom;
$A^4$ is a hydrogen atom;
$A^5$ is a methoxy group;
M is a sodium atom; and
n is 1.

In another embodiment, further preferred specific combinations of $A^1, A^2, A^3, A^4, A^5$, M and n in the general formula (4) are:
$A^1$ is a methoxy group;
$A^2$ is a hydrogen atom;
$A^3$ is a methoxy group;
$A^4$ is a hydrogen atom;
$A^5$ is a methoxy group;
M is a sodium atom; and
n is 1.

Particularly preferred specific combinations of $A^1, A^2, A^3, A^4, A^5$, M and n in the general formula (4) are:
$A^1$ is a methoxy group;
$A^2$ is a hydrogen atom;
$A^3$ is a hydrogen atom;
$A^4$ is a hydrogen atom;
$A^5$ is a methoxy group;
M is a sodium atom; and n is 1.

Specific examples of benzoic acid compounds and related benzoic acid compounds and other benzoic acid compounds used in examples and comparative examples of the present invention are shown below;

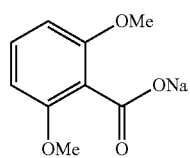

(4-1)

-continued

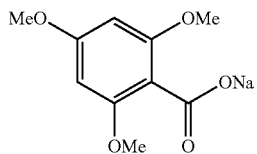

(4-2)

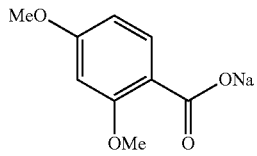

(4-3)

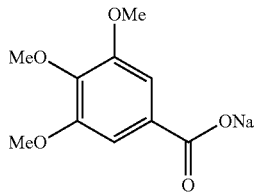

(4-4)

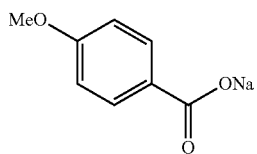

(4-5)

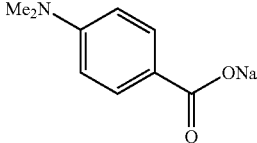

(4-6)

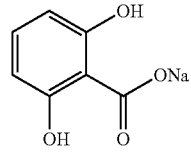

(4-7)

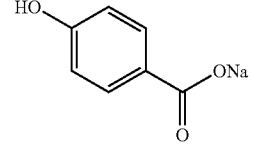

(4-8)

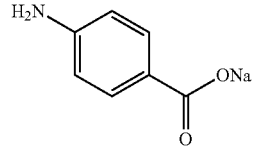

(4-9)

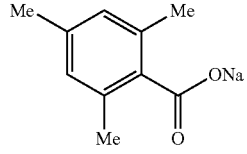

(4-10)

(4-11) 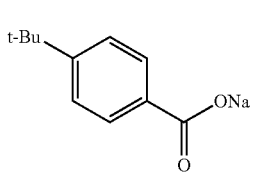

(4-12) 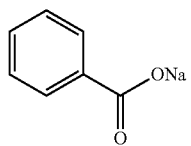

(4-13) 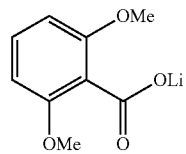

(4-14) 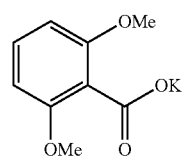

(4-15) 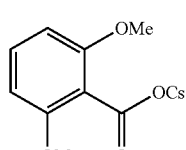

(4-16) 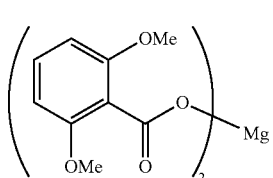

(4-17) 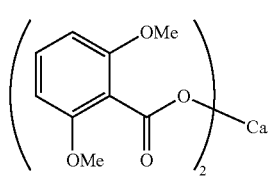

(4-18) 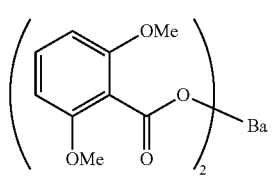

(4-19) 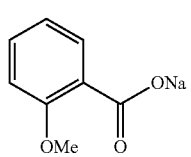

Preferred specific examples of the benzoic acid compound in the present invention include the compounds of the above formulas (4-1) and (4-2).

A particularly preferred specific example of the benzoic acid compound in the present invention is the compound of the above formula (4-1).

Generally in the oxidation reaction for producing the sulfoxide derivative (titled compound of the present invention) of the general formula (1) from the sulfide derivative (starting compound of the present invention) of the general formula (2), even if the benzoic acid compound of the general formula (4) is not used, the reaction can proceed. Therefore, as long as the reaction proceeds, the benzoic acid compound of the general formula (4) may or may not be used. However, from the viewpoint of improving the yield, etc., the benzoic acid compound of the general formula (4) is preferably used in the reaction of the present invention. In addition, from the viewpoint of reducing the amount of the catalyst (i.e. the amount of the metal compound and the amount of the ligand), the benzoic acid compound of the general formula (4) is preferably used in the reaction of the present invention. In other words, the reaction of the present invention is preferably carried out in the presence of the benzoic acid compound of the general formula (4).

By using the benzoic acid compound represented by the general formula (4), advantageous effects of the present invention were obtained. In this context, the most preferred combinations of $R^1$, $R^2$, $R^3$, $R^4$, $R^5$, $R^6$, $R^{71}$, $R^{72}$, $A^1$, $A^2$, $A^3$, $A^4$, $A^5$, M and n in the present invention are combinations of the above-mentioned "particularly preferred specific combinations".

(The Amount of the Benzoic Acid Compound Represented by the General Formula (4) Used)

The amount of the benzoic acid compound represented by the general formula (4) used in the method of the present invention may be in any amount as long as the reaction proceeds. In one embodiment, from the viewpoint of yield and economic efficiency, etc., the use amount of the benzoic acid compound represented by the general formula (4) in the present invention is 0.1 to 20 mol %, preferably 3 to 20 mol %, more preferably 3 to 15 mol %, further preferably 3 to 10 mol %, particularly preferably 3 to 5 mol % based on 1 mol of the sulfide derivative (starting compound) represented by the general formula (2). Further, in another embodiment, from the same viewpoint as described above, the amount of the benzoic acid compound represented by the general formula (4) used in the present invention is preferably 1 to 20 mol %, more preferably 1 to 15 mol %, still more preferably 1 to 10 mol %, particularly preferably 1 to 5 mol % based on 1 mol of the sulfide derivative (starting compound) represented by the general formula (2). However, the use amount of the benzoic acid compound represented by the general formula (4) in the present invention can be appropriately adjusted by those skilled in the art depending on the purpose and the situation.

(Preparation of Catalyst Solution)

A catalyst solution can be prepared by stirring a metal compound and a compound represented by the general formula (3) as a ligand, and a benzoic acid compound represented by the general formula (4) in a predetermined solvent. As the solvent in the preparation of the catalyst solution of the present invention, the following solvent "solvent in the reaction of the present invention" can be mentioned. The temperature in the preparation of the catalyst solution of the present invention is not particularly limited, but can be exemplified in the range of 0° C. to 50° C., preferably 15 to 30° C. (room temperature) from the viewpoint of catalyst stability and the like. The time in the preparation of the catalyst solution of the present invention is not particularly limited, but from the viewpoint of stability of the catalyst and the like, it can be exemplified within the range of 10 minutes to 12 hours, more preferably 10 minutes to 2 hours, further preferably 10 minutes to 1 hour. Specific examples thereof include 30 minutes, 1 hour and 2 hours, preferably 30 minutes and 1 hour, more preferably 30 minutes. However, as long as the reaction proceeds, the method for preparing the catalyst solution can be appropriately selected and adjusted by those skilled in the art.

(Method for Producing Sulfoxide Derivative)

The sulfoxide derivative represented by the general formula (1) can be produced by reacting the sulfide derivative represented by the general formula (2) with the catalyst solution prepared above and the oxidizing agent in a predetermined solvent. However, as long as the reaction proceeds, the method of the present invention is not limited to the examples and the method of preparing the catalyst solution as described above. The order of addition of raw materials, reagents, solvents and the like can be appropriately selected and adjusted by those skilled in the art.

(Solvent)

From the viewpoint of smooth proceeding of the reaction and the like, the reaction of the present invention is preferably carried out in the presence of a solvent. The solvent in the reaction of the present invention may be any solvent as long as the reaction proceeds.

The examples of the solvent in the reaction of the present invention include, but are not limited to, Water, Halogenated aliphatic hydrocarbons (for example, dichloromethane, chloroform, carbon tetrachloride, 1,2-dichloroethane, 1,3-dichloropropane, 1,4-dichlorobutane, trichloroethane, trichlorethylene, tetrachloroethane, tetrachlorethylene, pentachloroethane, etc., preferably dichloromethane, chloroform, carbon tetrachloride, 1,2-dichloroethane, more preferably dichloromethane)

Aromatic hydrocarbon derivatives (for example, benzene, toluene, xylene, trimethylbenzene, chlorobenzene, dichlorobenzene, trichlorobenzene, chlorotoluene, benzotrifluoride, 4-chlorobenzotrifluoride, difluorobenzene, bromobenzene, nitrobenzene and the like, Preferably toluene, xylene, chlorobenzene, dichlorobenzene, chlorotoluene), Nitriles (for example, acetonitrile, propionitrile, butyronitrile and the like, preferably acetonitrile), carboxylic acid esters (for example, ethyl acetate, isopropyl acetate, butyl acetate etc.), amides (for example, N,N-dimethylformamide (DMF), N,N-dimethylacetamide (DMAC), N,N-diethylacetamide, N-methylpyrrolidone (NMP) and the like, preferably N,N-dimethylformamide (DMF), N,N-dimethylacetamide (DMAC), N-methylpyrrolidone (NMP), more preferably N,N-dimethylformamide (DMF)), Alkylureas (for example, N,N'-dimethylimidazolidinone (DMI), etc.), sulfoxides (for example, dimethylsulfoxide (DMSO), etc.)

Sulfones (for example, sulfolane etc.), carbonate esters (for example, ethylene carbonate, propylene carbonate, etc.)

Alcohols (for example, methanol, ethanol, propanol, 2-propanol, butanol, ethylene glycol and the like), Ethers (for example, tetrahydrofuran (THF), 2-methyltetrahydrofuran, 1,4-dioxane, diethyl ether, diisopropyl ether, dibutyl ether, di-tert-butyl ether, cyclopentyl methyl ether (CPME), methyl tert-butyl ether (MTBE), tert-amyl methyl ether (TAME), 1,2-dimethoxyethane (DME), diglyme, triglyme, 4-methoxybenzene, diphenyl ether, etc.) and any combination thereof in any proportion.

From the viewpoint of reactivity and economic efficiency, etc., preferred examples of solvents include water, halogenated aliphatic hydrocarbons, aromatic hydrocarbon derivatives, nitriles, carboxylic acid esters, amides, and any combination thereof in any proportion.

More preferred examples of solvents include water, halogenated aliphatic hydrocarbons, aromatic hydrocarbon derivatives, nitriles, amides, and any combination thereof in any proportion.

Further preferred examples of solvents include water, halogenated aliphatic hydrocarbons, aromatic hydrocarbon derivatives, and any combination thereof in any proportion.

Particularly preferred examples of solvents include water, halogenated aliphatic hydrocarbons, and any combination thereof in any proportion.

Preferred specific examples of the solvent are water, dichloromethane, chloroform, carbon tetrachloride, 1,2-dichloroethane, toluene, xylene, chlorobenzene, dichlorobenzene, chlorotoluene, acetonitrile, ethyl acetate, isopropyl acetate, butyl acetate, N,N-dimethylformamide (DMF), N,N-dimethylacetamide (DMAC), N-methylpyrrolidone (NMP), and any proportions thereof in any proportion.

More preferable examples of the solvent include water, dichloromethane, chloroform, carbon tetrachloride, 1,2-dichloroethane, toluene, xylene, chlorobenzene, dichlorobenzene, acetonitrile, N,N-dimethylformamide (DMF) and any combination thereof in any proportion.

Further preferred examples of solvents include water, dichloromethane, chloroform, carbon tetrachloride, 1,2-dichloroethane, toluene, xylene, chlorobenzene, dichlorobenzene, and any combination thereof in any proportion.

Particularly preferred examples of the solvent include water, dichloromethane, and any combination thereof in any proportion. However, the solvent in the reaction of the present invention can be appropriately selected by those skilled in the art.

The amount of the solvent to be used may be any amount as long as the reaction proceeds. 0.01 to 10.0 L (liter), preferably 0.1 to 5.0 L, based on 1 mol of the sulfide derivative (starting compound) represented by the general formula (2) can be exemplified from the viewpoints of improvement of yield, suppression of byproducts, economic efficiency and the like. However, the amount of solvent used in the reaction of the present invention can be appropriately adjusted by those skilled in the art. When a combination of two or more solvents is used, the ratio of two or more kinds of solvents may be any proportion as long as the reaction proceeds.

(Reaction Temperature)

The reaction temperature of the present invention is not particularly limited. In one embodiment, from the viewpoints of improvement of yield, suppression of byproducts, economic efficiency, and the like, it is preferably from −20° C. to 50° C. (i.e., from minus 20° C. to plus 50° C.), preferably from −10° C. to 30° C. (i.e., minus 10° C. to plus 30° C.), more preferably from −10° C. to 20° C. (i.e., minus 10° C. to plus 20° C.), further preferably −5° C. to 15° C.(i.e., minus 5° C. Plus 15° C.), particularly preferably in the range of 0° C. to 10° C. (i.e., 0° C. to plus 10° C.). In another embodiments, from the viewpoint same as the above, it is preferable that the temperature is in the range of −20° C. to 50° C. (i.e., minus 20° C. to plus 50° C.), preferably −10° C. to 40° C. (i.e., minus 10° C. to plus 40° C.) More preferably -5° C. to 40° C. (i.e., minus 5° C. to plus 40° C.), further preferably −5° C. to 30° C. (i.e., minus 5° C. to plus 30° C.), particularly preferably 0° C. to 10° C. (i.e., from 0° C. to plus 10° C.) can also be exemplified.

(Reaction Time)

The reaction time of the present invention is not particularly limited. In one embodiment, from the viewpoints of improvement of yield, suppression of byproducts, economic efficiency and the like, it is preferable that the reaction time is 0.5 hour to 120 hours, preferably 1 hour to 72 hours, more preferably 1 hour to 48 hours, further preferably in the range of 1 hour to 24 hours. In another embodiment, from the same viewpoint as described above, a range of 6 hours to 120 hours, preferably 8 hours to 72 hours, more preferably 8 hours to 48 hours, further preferably 8 hours to 24 hours can also be exemplified. However, the reaction time of the present invention can be appropriately adjusted by those skilled in the art.

(Reaction Yield and Yield)

In the present specification, the terms "reaction yield" and "yield" respectively have the following meanings.

(Reaction Yield)

In the present invention, the reaction yield was determined by analyzing the organic layer of the reaction mixture by the following HPLC analysis condition (A). In the present specification, the reaction yield is indicated by the HPLC area percentage of titled compound.

The reaction yield in the present invention is preferably in the range of 90 to 100%, more preferably 95 to 100%.

(Yield)

The yield in the present invention can be calculated from the number of moles of the sulfoxide compound (objective compound) represented by the general formula (1) obtained, based on the number of moles of the sulfide derivative (Raw material compound) represented by the general formula (2). That is, the yield in the present invention is represented by the following formula:

Yield (%)=(number of moles of the obtained titled compound)/(number of moles of the starting compound)×100

The yield in the present invention is preferably in the range of 90 to 100%, for example.

Hereinafter, the present invention will be described in more detail with reference to examples, but the present invention is not limited by these examples at all.

In the present specification, the following equipment and conditions were used for measuring the physical properties of the examples and comparative examples.

(HPLC: High Performance Liquid Chromatography)
(HPLC analysis condition (A))
Pump: LC-20AT (manufactured by Shimadzu Corporation)
Detector: SPD-20A (manufactured by Shimadzu Corporation)
Column: CERI L-column ODS (4.6×250 mm), L-C18, 5 μm, 12 nm
Eluent:

| time (minute) | acetonitrile (%) | 0.5% phosphoric acid aqueous solution(%) |
|---|---|---|
| 0 | 40 | 60 |
| 5 | 40 | 60 |
| 15 | 100 | 0 |
| 25 | 100 | 0 |

Flow rate: 1.0 ml/min
Detection: UV 254 nm
Column temperature: 40° C.

As described above, in the evaluation of the reaction yield, the area percentage according to the above HPLC analysis condition (A) was used.

Regarding the HPLC analysis method, the following documents can be referred to if necessary.

Document (a): edited by The Chemical Society of Japan, "New Experimental Chemistry Course 9 Analytical Chemistry II", pages 86 to 112 (1977), issuer Shingo Iizumi, Maruzen Co., Ltd.

Document (b): edited by The Chemical Society of Japan, "Experimental Chemistry Course 20-1 Analytical Chemistry", 5th edition, pages 130 to 151 (2007), issuer Seijiro Murata, Maruzen Co., Ltd.

($^1$H-NMR: $^1$H nuclear magnetic resonance spectrum; analysis condition (A))
Equipment: JEOL JMN-ECS-300 or JEOL JMN-Lambda-400 (manufactured by JEOL RESONANCE, INC.)
Internal standard substance: tetramethylsilane (TMS)
(LC/MS: liquid chromatographic mass spectrometry)
(LC/MS analysis condition)
Pump: Waters Acquity H Class
Detector: Waters Q-Tof Premier
Column: CERI L-column ODS (4.6×250 mm), L-C18, 5 μm, 12 nm Eluent:

| time (minute) | acetonitrile (%) | 0.5% phosphoric acid aqueous solution(%) |
|---|---|---|
| 0 | 40 | 60 |
| 5 | 40 | 60 |
| 15 | 100 | 0 |
| 25 | 100 | 0 |

Flow rate: 1.0 ml/min
Column temperature: 40° C.

In examples and comparative examples of the present invention, as a reaction vessel in preparation of a catalyst solution and production of titled compound, a reaction vessel which is usually used by those skilled in the art was used. For example, approximately 6 mL screw vials (vial with screw cap) with an inner diameter of 15 mm and a height of 40 mm equipped with a cross-shaped magnetic stirrer having an outer diameter (length) of 10 mm and a height (thickness) of 5 mm and a magnetic stirrer with a thermostat was used.

In the present specification, the room temperature is 15° C. to 30° C.

EXAMPLE 1

Production of 5-trifluoromethylthiopentyl-[4-chloro-2-fluoro-5-(2,2,2-trifluoroethylsulfinyl)phenyl] ether

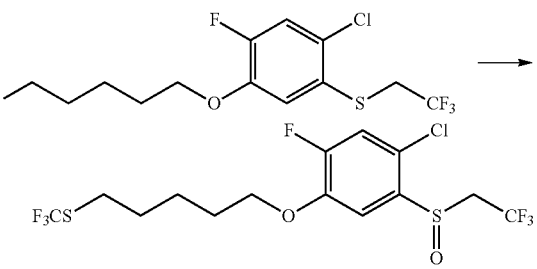

(1) Preparation of Catalyst Solution

Fe(acac)₃ (1.8 mg, 0.005 mmol), a compound of formula (3-4) (1.0 mg, 0.005 mmol), the compound of formula (4-1) (sodium 2,6-dimethoxybenzoate; 5.1 mg, 0.025 mmol) and dichloromethane (1 mL) were added to avial eqquipped with a screw cap. The mixture was stirred at room temperature for 30 minutes.

(2) Production of Titled Compound

5-Trifluoromethylthiopentyl-[4-chloro-2-fluoro-5 -(2,2,2-trifluoroethylthio)phenyl ] ether (215.4 mg, 0.500 mmol) was dissolved in dichloromethane (1.0 mL). The catalyst solution prepared in (1) above was added thereto. The mixture was cooled to 0° C. 30% hydrogen peroxide (113.4 mg, 1.0 mmol) was added thereto. The mixture was stirred at 0° C. for 14h. The organic layer of the reaction mixture was analyzed by HPLC (area percentage). As a result, the components excluding the solvent etc. in the reaction mixture were as follows;

5-trifluoromethylthiopentyl-[4-chloro-2-fluoro-5-(2,2,2-trifluoroethylsulfinyl)phenyl] ether (titled compound): 98%, 5-trifluoromethylthiopentyl-[4-chloro-2-fluoro-5-(2,2,2-trifluoroethylthio)phenyl]ether (starting compound): 0%, 5-trifluoromethylthiopentyl-[4-chloro-2-fluoro-5-(2,2,2-trifluoroethylsulfonyl)phenyl] ether (byproduct by excess oxidation): 0%.

EXAMPLE 2

Production of 5-trifluoromethylthiopentyl-[4-chloro-2-fluoro-5-(2,2,2-trifluoroethylsulfinyl)phenyl] ether

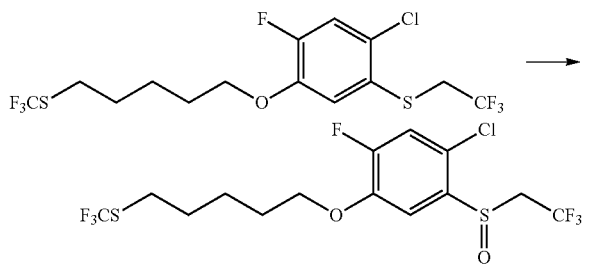

(1) Preparation of Catalyst Solution

Fe(acac)₃ (1.8 mg, 0.005 mmol), a compound of the formula (3-4) (1.0 mg, 0.005 mmol), a compound of the formula (4-1) (Sodium 2,6 -dimethoxybenzoate; 5.1 mg, 0.025 mmol), and dichloromethane (1 mL) were added to a vial equipped with a screw cap. The mixture was stirred at room temperature for 30 minutes.

(2) Production of Titled Compound

5-Trifluoromethylthiopentyl-[4-chloro-2-fluoro-5-(2,2,2-trifluoroethylthio)phenyl ]ether (215.4 mg, 0.500 mmol) was dissolved in dichloromethane (1.0 mL). The catalyst solution prepared in (1) above was added thereto. The mixture was cooled to 0° C. 30% hydrogen peroxide (113.4 mg, 1.0 mmol) was added thereto. The mixture was stirred at 0° C. for 15 h. The organic layer of the reaction mixture was analyzed by HPLC (area percentage). As a result, the components excluding the solvent etc. in the reaction mixture were as follows;

5-trifluoromethylthiopentyl-[4-chloro-2-fluoro-5-(2,2,2-trifluoroethylsulfinyl)phenyl] ether (titled compound): 98%, 5-trifluoromethylthiopentyl-[4-chloro-2-fluoro-5-(2,2,2-trifluoroethylthio)phenyl]ether (starting compound): 0%, 5-trifluoromethylthiopentyl-[4-chloro-2-fluoro-5-(2,2,2-trifluoroethylsulfonyl)phenyl] ether (byproduct by excess oxidation): 0%.

To the reaction mixture was added aqueous sodium hydrogen sulfite solution and the mixture was stirred at room temperature for 5 minutes. The mixture was partitioned between organic and aqueous layers and the organic layer was separated. Sodium hydrogen carbonate was added to the obtained organic layer, and the mixture was stirred at room temperature for 5 minutes. The mixture was partitioned between organic and aqueous layers and the organic layer was separated. The obtained organic layer was dried over anhydrous magnesium sulfate and concentrated under reduced pressure to obtain 214.2 mg of titled compound (HPLC purity 97.6%).

Purity conversion yield (yield in terms of purity): 94%.

¹H-NMR (400 MHz, CDCl₃) δ (ppm, TMS standard): 1.57-1.66 (m, 2H), 1.74-1.93 (m, 4H), 2.92 (t, 2H), 3.30-3.43 (m, 1H), 3.66-3.78 (m, 1H), 4.13 (t, 2H), 7.21 (d, 1H), 7.54, (d, 1H)

EXAMPLE 3

Production of 5-trifluoromethylthiopentyl-[4-chloro-2-fluoro-5-(2,2,2-trifluoroethylsulfinyl)phenyl] ether

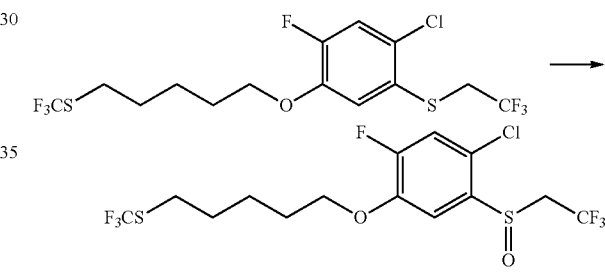

(1) Preparation of Catalyst Solution

Fe(acac)₃ (5.3 mg, 0.015 mmol), a compound of the formula (3-12) (3.6 mg, 0.015 mmol), a compound of the formula (4-1) (Sodium 2,6-dimethoxybenzoate; 15.3 mg, 0.075 mmol), and dichloromethane (1 mL) were added to a vial equipped with a screw cap. The mixture was stirred at room temperature for 30 minutes.

(2) Production of Titled Compound

5-Trifluoromethylthiopentyl-[4-chloro-2-fluoro-5-(2,2,2-trifluoroethylthio) phenyl]ether (215.4 mg, 0.500 mmol) was dissolved in dichloromethane (1.0 mL). The catalyst solution prepared in (1) above was added thereto. The mixture was cooled to 0° C. 30% hydrogen peroxide (113.4 mg, 1.0 mmol) was added thereto. The mixture was stirred at 0° C. for 60 h. The organic layer of the reaction mixture was analyzed by HPLC (area percentage). As a result, the components excluding the solvent etc. in the reaction mixture were as follows;

5-trifluoromethylthiopentyl-[4-chloro-2-fluoro-5-(2,2,2-trifluoroethylsulfinyl)phenyl] ether (titled compound): 96%, 5-trifluoromethylthiopentyl-[4-chloro-2-fluoro-5-(2,2,2-trifluoroethylthio)phenyl]ether (starting compound): 0%, 5-trifluoromethylthiopentyl-[4-chloro-2-fluoro-5-(2,2,2-trifluoroethylsulfonyl)phenyl] ether (byproduct by excess oxidation): 0%.

EXAMPLE 4

Production of 5-trifluoromethylthiopentyl-[4-chloro-2-fluoro-5-(2,2,2-trifluoroethylsulfinyl)phenyl] ether

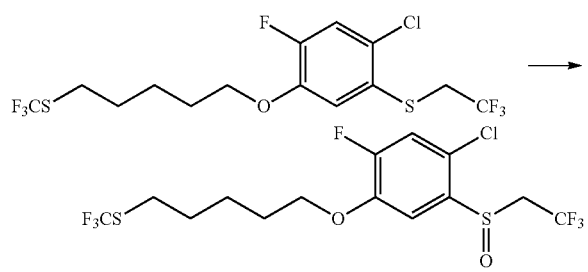

(1) Preparation of Catalyst Solution

Fe(acac)₃ (1.8 mg, 0.005 mmol), the compound of the formula (3-9) (1.1 mg, 0.005 mmol), the compound of the formula (4-1) (Sodium 2,6-dimethoxybenzoate; 5.1 mg, 0.025 mmol), and dichloromethane (1 mL) were added to a vial equipped with a screw cap. The mixture was stirred at room temperature for 30 minutes.

(2) Production of Titled Compound

5-Trifluoromethylthiopentyl-[4-chloro-2-fluoro-5-(2,2,2-trifluoroethylthio)phenyl] ether (215.4 mg, 0.500 mmol) was dissolved in dichloromethane (1.0 mL). The catalyst solution prepared in (1) above was added thereto. The mixture was cooled to 0° C. 30% hydrogen peroxide (113.4 mg, 1.0 mmol) was added thereto. The mixture was stirred at 0° C. for 22 h. The organic layer of the reaction mixture was analyzed by HPLC (area percentage). As a result, the components excluding the solvent etc. in the reaction mixture were as follows;

5-trifluoromethylthiopentyl-[4-chloro-2-fluoro-5-(2,2,2-trifluoroethylsulfinyl)phenyl] ether (titled compound): 97%,
5-trifluoromethylthiopentyl-[4-chloro-2-fluoro-5-(2,2,2-trifluoroethylthio)phenyl]ether (starting compound): 0%,
5-trifluoromethylthiopentyl-[4-chloro-2-fluoro-5-(2,2,2-trifluoroethylsulfonyl)phenyl] ether (byproduct by excess oxidation): 0%.

EXAMPLE 5

Production of 5-trifluoromethylthiopentyl-[4-chloro-2-fluoro-5-(2,2,2-trifluoroethylsulfinyl)phenyl] ether

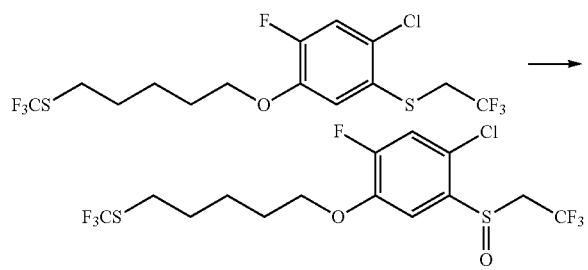

(1) Preparation of Catalyst Solution 2,6-Dimethoxybenzoic acid (4.6 mg, 0.025 mmol), sodium hydroxide powder (1.0 mg, 0.025 mmol), and dichloromethane (1 mL) were added to a vial equipped with a screw cap. The mixture was stirred at room temperature for 30 minutes. Fe (acac)₃ (1.8 mg, 0.005 mmol) and the compound of formula (3-9) (1.1 mg, 0.005 mmol) were added to the solution. The mixture was stirred at room temperature for 30 minutes.

(2) Production of Titled Compound

5-Trifluoromethylthiopentyl-[4-chloro-2-fluoro-5-(2,2,2-trifluoroethylthio)phenyl]ether (215.4 mg, 0.500 mmol) was dissolved in dichloromethane (1.0 mL). The catalyst solution prepared in (1) above was added thereto. The mixture was cooled to 0° C. 30% hydrogen peroxide (113.4 mg, 1.0 mmol) was added thereto. The mixture was stirred at 0° C. for 21 h. The organic layer of the reaction mixture was analyzed by HPLC (area percentage). As a result, the components excluding the solvent etc. in the reaction mixture were as follows;

5-trifluoromethylthiopentyl-[4-chloro-2-fluoro-5-(2,2,2-trifluoroethylsulfinyl)phenyl] ether (titled compound): 96%,
5-trifluoromethylthiopentyl-[4-chloro-2-fluoro-5-(2,2,2-trifluoroethylthio)phenyl]ether (starting compound): 0%,
5-trifluoromethylthiopentyl-[4-chloro-2-fluoro-5-(2,2,2-trifluoroethylsulfonyl)phenyl] ether (byproduct by excess oxidation): 0%.

EXAMPLE 6

Production of 5-trifluoromethylthiopentyl-[4-chloro-2-fluoro-5-(2,2,2-trifluoroethylsulfinyl)phenyl] ether

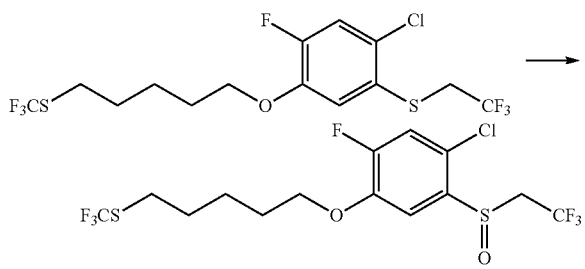

(1) Preparation of Catalyst Solution

Fe(acac)₃ (1.8 mg, 0.005 mmol), a compound of the formula (3-4) (1.0 mg, 0.005 mmol), a compound of the formula (4-1) (Sodium 2,6-dimethoxybenzoate; 5.1 mg, 0.025 mmol), and dichloromethane (1 mL) were added to a vial equipped with a screw cap. The mixture was stirred at room temperature for 30 minutes.

(2) Production of Titled Compound

5-Trifluoromethylthiopentyl-[4-chloro-2-fluoro-5-(2,2,2-trifluoroethylthio)phenyl]ether (215.4 mg, 0.500 mmol) was dissolved in dichloromethane (1.0 mL). The catalyst solution prepared in (1) above was added thereto. The mixture was cooled to 0° C. 30% hydrogen peroxide (113.4 mg, 1.0 mmol) was added thereto. The mixture was stirred at 10° C. for 14 h. The organic layer of the reaction mixture was analyzed by HPLC (area percentage). As a result, the components excluding the solvent etc. in the reaction mixture were as follows;

5-trifluoromethylthiopentyl-[4-chloro-2-fluoro-5-(2,2,2-trifluoroethylsulfinyl)phenyl] ether (titled compound): 98%,
5-trifluoromethylthiopentyl-[4-chloro-2-fluoro-5-(2,2,2-trifluoroethylthio)phenyl]ether (starting compound): 0%, 5-trifluoromethylthiopentyl-[4-chloro-2-fluoro-5-(2,2,2-tri-fluoroethylsulfonyl)phenyl] ether (byproduct by excess oxidation): 0%.

EXAMPLE 7

Production of 5-trifluoromethylthiopentyl-[4-chloro-2-fluoro-5-(2,2,2-trifluoroethylsulfinyl)phenyl] ether

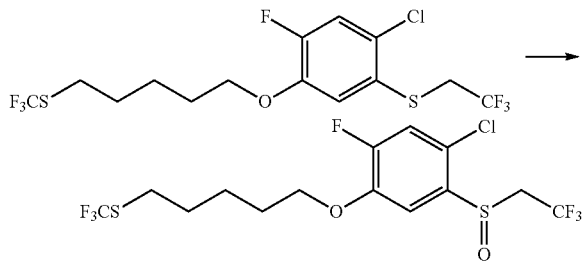

(1) Preparation of Catalyst Solution

Fe(acac)$_3$ (1.8 mg, 0.005 mmol), a compound of the formula (3-4) (1.0 mg, 0.005 mmol), a compound of the formula (4-1) (Sodium 2,6-dimethoxybenzoate; 5.1 mg, 0.025 mmol), and dichloromethane (1 mL) were added to a vial equipped with a screw cap. The mixture was stirred at room temperature for 30 minutes.

(2) Production of Titled Compound

5-Trifluoromethylthiopentyl-[4-chloro-2-fluoro-5-(2,2,2-trifluoroethylthio)phenyl ] ether (215.4 mg, 0.500 mmol) was dissolved in dichloromethane (1.0 mL). The catalyst solution prepared in (1) above was added thereto. The mixture was cooled to 0° C. 30% hydrogen peroxide (113.4 mg, 1.0 mmol) was added thereto. The mixture was stirred at 20° C. for 36 h. The organic layer of the reaction mixture was analyzed by HPLC (area percentage). As a result, the components excluding the solvent etc. in the reaction mixture were as follows;

5-trifluoromethylthiopentyl-[4-chloro-2-fluoro-5-(2,2,2-tri-fluoroethylsulfinyl)phenyl] ether (titled compound): 94%, 5-trifluoromethylthiopentyl-[4-chloro-2-fluoro-5-(2,2,2-tri-fluoroethylthio)phenyl]ether (starting compound): 4%, 5-trifluoromethylthiopentyl-[4-chloro-2-fluoro-5-(2,2,2-tri-fluoroethylsulfonyl)phenyl] ether (byproduct by excess oxidation): 0%.

(3) Production of Titled Compound Using Additional Hydrogen Peroxide

To the reaction mixture obtained above, 30% hydrogen peroxide (56.7 mg, 0.5 mmol) was added. The mixture was stirred at 20° C. for 15 h. The organic layer of the reaction mixture was analyzed by HPLC (area percentage). As a result, the components excluding the solvent etc. in the reaction mixture were as follows;

5-trifluoromethylthiopentyl-[4-chloro-2-fluoro-5-(2,2,2-tri-fluoroethylsulfinyl)phenyl] ether (titled compound): 94%, 5-trifluoromethylthiopentyl-[4-chloro-2-fluoro-5-(2,2,2-tri-fluoroethylthio)phenyl]ether (starting compound): 4%, 5-trifluoromethylthiopentyl-[4-chl oro-2-fluoro-5-(2,2,2-tri-fluoroethylsulfonyl)phenyl] ether (byproduct by excess oxidation): 0%.

COMPARATIVE EXAMPLE 1

Production of 5-trifluoromethylthiopentyl-[4-chloro-2-fluoro-5-(2,2,2-trifluoroethylsulfinyl)phenyl] ether

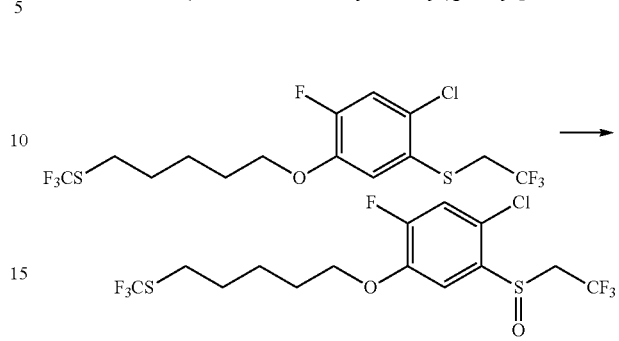

(1) Preparation of Catalyst Solution

Fe(acac)$_3$ (1.8 mg, 0.005 mmol), a compound of the formula (3-13) (1.0 mg, 0.005 mmol), a compound of the formula (4-1) (Sodium 2,6-dimethoxybenzoate; 5.1 mg, 0.025 mmol), and dichloromethane (1 mL) were added to a vial equipped with a screw cap. The mixture was stirred at room temperature for 30 minutes.

(2) Production of Titled Compound

5-Trifluoromethylthiopentyl-[4-chloro-2-fluoro-5-(2,2,2-trifluoroethylthio)phenyl] ether (215.4 mg, 0.500 mmol) was dissolved in dichloromethane (1.0 mL). The catalyst solution prepared in (1) above was added thereto. The mixture was cooled to 0° C. 30% hydrogen peroxide (113.4 mg, 1.0 mmol) was added thereto. The mixture was stirred at 0° C. for 15 h. The organic layer of the reaction mixture was analyzed by HPLC (area percentage). As a result, the components excluding the solvent etc. in the reaction mixture were as follows;

5-trifluoromethylthiopentyl-[4-chloro-2-fluoro-5-(2,2,2-tri-fluoroethylsulfinyl)phenyl] ether (titled compound): 14%, 5-trifluoromethylthiopentyl-[4-chloro-2-fluoro-5-(2,2,2-tri-fluoroethylthio)phenyl]ether (starting compound): 83%, 5-trifluoromethylthiopentyl-[4-chloro-2-fluoro-5-(2,2,2-tri-fluoroethylsulfonyl)phenyl] ether (byproduct by excess oxidation): 0%.

(3) Preparation of Additional Catalyst Solution

Fe(acac)$_3$ (5.4 mg, 0.015 mmol), the compound of the formula (3-13) (3.0 mg, 0.015 mmol), the compound of the formula (4-1) (Sodium 2,6-dimethoxybenzoate; 5.1 mg, 0.025 mmol), and dichloromethane (1 mL) were added to a vial equipped with a screw cap. The mixture was stirred at room temperature for 30 minutes.

(4) Production of Titled Compound Using Additional Catalyst and Additional Hydrogen Peroxide To the reaction mixture obtained in the above (2), the catalyst solution prepared in (3) above was added continuously at 0° C. 30% hydrogen peroxide (56.7 mg, 0.5 mmol) was added thereto. The mixture was stirred at 0° C. for 8 h. The organic layer of the reaction mixture was analyzed by HPLC (area percentage). As a result, the components excluding the solvent etc. in the reaction mixture were as follows;

5-trifluoromethylthiopentyl-[4-chloro-2-fluoro-5-(2,2,2-tri-fluoroethylsulfinyl)phenyl] ether (titled compound): 23%, 5-trifluoromethylthiopentyl-[4-chloro-2-fluoro-5-(2,2,2-tri-fluoroethylthio)phenyl]ether (starting compound): 74%, 5-trifluoromethylthiopentyl-[4-chloro-2-fluoro-5-(2,2,2-tri-
fluoroethylsulfonyl)phenyl] ether (byproduct by excess
oxidation): 0%.

COMPARATIVE EXAMPLE 2

Production of 5-trifluoromethylthiopentyl-[4-chloro-
2-fluoro-5-(2,2,2-trifluoroethylsulfinyl)phenyl] ether

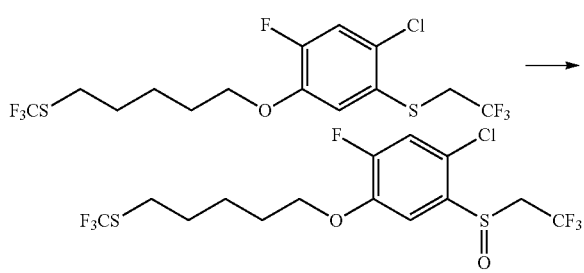

(1) Preparation of Catalyst Solution
Fe(acac)$_3$ (1.8 mg, 0.005 mmol), a compound of the formula (3-4) (1.0 mg, 0.005 mmol), a compound of the formula (4-19) (Sodium 2-methoxy benzoate; 4.4 mg, 0.025 mmol), and dichloromethane (1 mL) were added to a vial equipped with a screw cap. The mixture was stirred at room temperature for 30 minutes.
(2) Production of Titled Compound
5-Trifluoromethylthiopentyl-[4-chloro-2-fluoro-5-(2,2,2-trifluoroethylthio)phenyl ]ether (215.4 mg, 0.500 mmol) was dissolved in dichloromethane (1.0 mL). The catalyst solution prepared in (1) above was added thereto. The mixture was cooled to 0° C. 30% hydrogen peroxide (113.4 mg, 1.0 mmol) was added thereto. The mixture was stirred at 0° C. for 14 h. The organic layer of the reaction mixture was analyzed by HPLC (area percentage). As a result, the components excluding the solvent etc. in the reaction mixture were as follows;
5-trifluoromethylthiopentyl-[4-chloro-2-fluoro-5-(2,2,2-tri-
fluoroethylsulfinyl)phenyl] ether (titled compound): 20%,
5-trifluoromethylthiopentyl-[4-chloro-2-fluoro-5-(2,2,2-tri-
fluoroethylthio)phenyl]ether (starting compound): 77%,
5-trifluoromethylthiopentyl-[4-chloro-2-fluoro-5-(2,2,2-tri-
fluoroethylsulfonyl)phenyl] ether (byproduct by excess
oxidation): 0%.

COMPARATIVE EXAMPLE 3

Production of 5-trifluoromethylthiopentyl-[4-chloro-
2-fluoro-5-(2,2,2-trifluoroethylsulfinyl)phenyl] ether

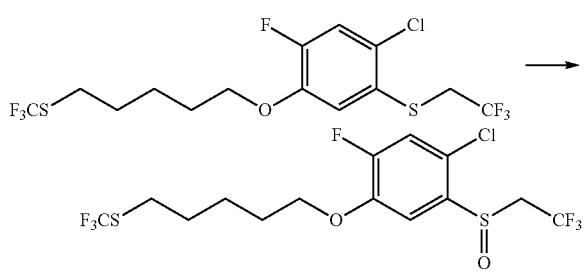

(1) Preparation of Catalyst Solution
Fe(acac)$_3$ (1.8 mg, 0.005 mmol), a compound of the formula (3-4) (1.0 mg, 0.005 mmol), a compound of the formula (4-5) (Sodium 4-methoxy benzoate; 4.4 mg, 0.025 mmol), and dichloromethane (1 mL) were added to a vial equipped with a screw cap. The mixture was stirred at room temperature for 30 minutes.
(2) Production of Titled Compound
5-Trifluoromethylthiopentyl-[4-chloro-2-fluoro-5-(2,2,2-trifluoroethylthio)phenyl]ether (215.4 mg, 0.500 mmol) was dissolved in dichloromethane (1.0 mL). The catalyst solution prepared in (1) above was added thereto. The mixture was cooled to 0° C. 30% hydrogen peroxide (113.4 mg, 1.0 mmol) was added thereto. The mixture was stirred at 0° C. for 16 h. The organic layer of the reaction mixture was analyzed by HPLC (area percentage). As a result, the components excluding the solvent etc. in the reaction mixture were as follows;
5-trifluoromethylthiopentyl-[4-chloro-2-fluoro-5-(2,2,2-tri-
fluoroethylsulfinyl)phenyl] ether (titled compound): 19%,
5-trifluoromethylthiopentyl-[4-chloro-2-fluoro-5-(2,2,2-tri-
fluoroethylthio)phenyl]ether (starting compound): 80%,
5-trifluoromethylthiopentyl-[4-chloro-2-fluoro-5-(2,2,2-tri-
fluoroethylsulfonyl)phenyl] ether (byproduct by excess
oxidation): 0%.

COMPARATIVE EXAMPLE 4

Production of 5-trifluoromethylthiopentyl-[4-chloro-
2-fluoro-5-(2,2,2-trifluoroethylsulfinyl)phenyl] ether

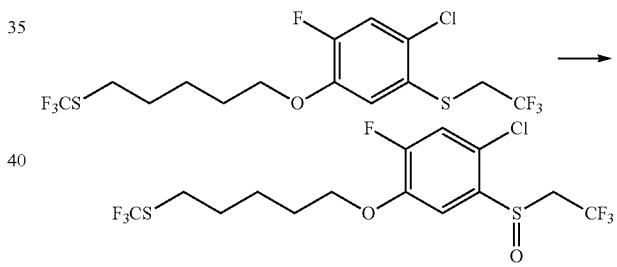

(1) Preparation of Catalyst Solution
Fe(acac)$_3$ (1.8 mg, 0.005 mmol), a compound of the formula (3-4) (1.0 mg, 0.005 mmol), a compound of the formula (4-12) (Sodium benzoate; 3.6 mg, 0.025 mmol), and dichloromethane (1 mL) were added to a vial equipped with a screw cap. The mixture was stirred at room temperature for 30 minutes.
(2) Production of Titled Compound
5-Trifluoromethylthiopentyl-[4-chloro-2-fluoro-5-(2,2,2-trifluoroethylthio)phenyl ]ether (215.4 mg, 0.500 mmol) was dissolved in dichloromethane (1.0 mL). The catalyst solution prepared in (1) above was added thereto. The mixture was cooled to 0° C. 30% hydrogen peroxide (113.4 mg, 1.0 mmol) was added thereto. The mixture was stirred at 0° C. for 16 h. The organic layer of the reaction mixture was analyzed by HPLC (area percentage). As a result, the components excluding the solvent etc. in the reaction mixture were as follows;
5-trifluoromethylthiopentyl-[4-chloro-2-fluoro-5-(2,2,2-tri-
fluoroethylsulfinyl)phenyl] ether (titled compound): 16%,
5-trifluoromethylthiopentyl-[4-chloro-2-fluoro-5-(2,2,2-tri-
fluoroethylthio)phenyl]ether (starting compound): 82%, 5-trifluoromethylthiopentyl-[4-chloro-2-fluoro-5-(2,2,2-trifluoroethylsulfonyl)phenyl] ether (byproduct by excess oxidation): 0%.

COMPARATIVE EXAMPLE 5

Production of 5-trifluoromethylthiopentyl-[4-chloro-2-fluoro-5-(2,2,2-trifluoroethylsulfinyl)phenyl] ether

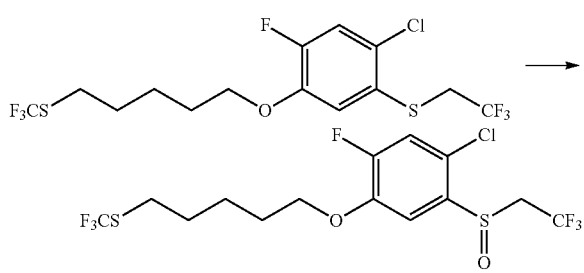

(1) Preparation of Catalyst Solution

Fe(acac)₃ (1.8 mg, 0.005 mmol), a compound of the formula (3-4) (1.0 mg, 0.005 mmol), sodium acetate (2.1 mg, 0.025 mmol) and dichloromethane (1 mL) were added to a vial equipped with a screw cap. The mixture was stirred at room temperature for 30 minutes.

(2) Production of Titled Compound

5-Trifluoromethylthiopentyl-[4-chloro-2-fluoro-5-(2,2,2-trifluoroethylthio)phenyl]ether (215.4 mg, 0.500 mmol) was dissolved in dichloromethane (1.0 mL). The catalyst solution prepared in (1) above was added thereto. The mixture was cooled to 0° C. 30% hydrogen peroxide (113.4 mg, 1.0 mmol) was added thereto. The mixture was stirred at 0° C. for 16 h. The organic layer of the reaction mixture was analyzed by HPLC (area percentage). As a result, the components excluding the solvent etc. in the reaction mixture were as follows;

5-trifluoromethylthiopentyl-[4-chloro-2-fluoro-5-(2,2,2-trifluoroethylsulfinyl)phenyl] ether (titled compound): 19%,
5-trifluoromethylthiopentyl-[4-chloro-2-fluoro-5-(2,2,2-trifluoroethylthio)phenyl]ether (starting compound): 79%,
5-trifluoromethylthiopentyl-[4-chloro-2-fluoro-5-(2,2,2-trifluoroethylsulfonyl)phenyl] ether (byproduct by excess oxidation): 0%.

COMPARATIVE EXAMPLE 6

Production of 5-trifluoromethylthiopentyl-[4-chloro-2-fluoro-5-(2,2,2-trifluoroethylsulfinyl)phenyl] ether

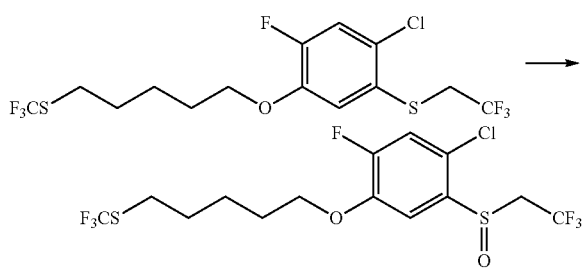

(1) Preparation of Catalyst Solution

Fe(acac)₃ (1.8 mg, 0.005 mmol), the compound of formula (3-4) (1.0 mg, 0.005 mmol), and dichloromethane (1 mL) were added to a vial equipped with a screw cap. The mixture was stirred at room temperature for 30 minutes.

(2) Production of Titled Compound

5-Trifluoromethylthiopentyl-[4-chloro-2-fluoro-5-(2,2,2-trifluoroethylthio)phenyl]ether (215.4 mg, 0.500 mmol) was dissolved in dichloromethane (1.0 mL). The catalyst solution prepared in (1) above was added thereto. The mixture was cooled to 0° C. 30% hydrogen peroxide (113.4 mg, 1.0 mmol) was added thereto. The mixture was stirred at 0° C. for 16 h. The organic layer of the reaction mixture was analyzed by HPLC (area percentage). As a result, the components excluding the solvent etc. in the reaction mixture were as follows;

5-trifluoromethylthiopentyl-[4-chloro-2-fluoro-5-(2,2,2-trifluoroethylsulfinyl) phenyl] ether (titled compound): 2%,
5-trifluoromethylthiopentyl-[4-chloro-2-fluoro-5-(2,2,2-trifluoroethylthio) phenyl] ether (starting compound): 96%,
5-trifluoromethylthiopentyl-[4-chloro-2-fluoro-5-(2,2,2-trifluoroethylsulfonyl) phenyl] ether (byproduct by excess oxidation): 0%.

COMPARATIVE EXAMPLE 7

Production of 5-trifluoromethylthiopentyl-[4-chloro-2-fluoro-5-(ethylsulfinyl)phenyl] ether

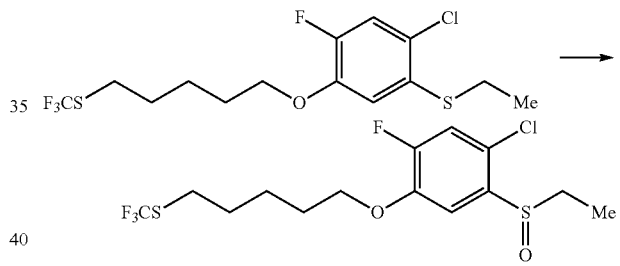

(1) Preparation of Catalyst Solution

Fe(acac)₃ (1.8 mg, 0.005 mmol), a compound of the formula (3-4) (1.0 mg, 0.005 mmol), a compound of the formula (4-1) (Sodium 2,6-dimethoxybenzoate; 5.1 mg, 0.025 mmol), and dichloromethane (1 mL) were added to a vial equipped with a screw cap. The mixture was stirred at room temperature for 30 minutes.

(2) Production of Titled Compound

5-Trifluoromethylthiopentyl-[4-chloro-2-fluoro-5-(ethylthio)phenyl] ether (188.4 mg, 0.500 mmol) was dissolved in dichloromethane (1.0 mL). The catalyst solution prepared in (1) above was added thereto. The mixture was cooled to 0° C. 30% hydrogen peroxide (113.4 mg, 1.0 mmol) was added thereto. The mixture was stirred at 0° C. for 24 h. The organic layer of the reaction mixture was analyzed by HPLC (area percentage). As a result, the components excluding the solvent etc. in the reaction mixture were as follows;

5-trifluoromethylthiopentyl-[4-chloro-2-fluoro-5-(ethylsulfinyl)phenyl]ether (titled compound): 39%,
5-trifluoromethylthiopentyl-[4-chloro-2-fluoro-5-(ethylthio)phenyl] ether (starting compound): 55%,
5-trifluoromethylthiopentyl-[4-chloro-2-fluoro-5-(ethylsulfonyl)phenyl]ether (byproduct by excess oxidation): 0%.
LC/MS (titled compound) of the product; Exact Mass: 392.0295, measured value (positive): 393.0370

COMPARATIVE EXAMPLE 8

Production of Methyl Phenyl Sulfoxide

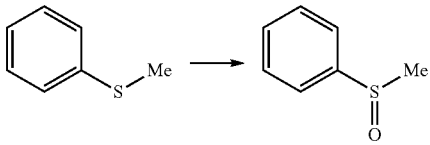 [SMILES: CSc1ccccc1 ; CS(=O)c1ccccc1]

(1) Preparation of Catalyst Solution

Fe(acac)₃ (1.8 mg, 0.005 mmol), a compound of the formula (3-4) (1.0 mg, 0.005 mmol), a compound of the formula (4-1) (Sodium 2,6-dimethoxybenzoate; 5.1 mg, 0.025 mmol), and dichloromethane (1 mL) were added to a vial equipped with a screw cap. The mixture was stirred at room temperature for 30 minutes.

(2) Production of Titled Compound

Thioanisole (62.1 mg, 0.500 mmol) was dissolved in dichloromethane (1.0 mL). The catalyst solution prepared in (1) above was added thereto. The mixture was cooled to 0° C. 30% hydrogen peroxide (113.4 mg, 1.0 mmol) was added thereto. The mixture was stirred at 0° C. for 20 h. The organic layer of the reaction mixture was analyzed by HPLC (area percentage). As a result, the components excluding the solvent etc. in the reaction mixture were as follows;
methyl phenyl sulfoxide (titled compound): 16%,
thioanisole (starting compound): 77%,
methylphenylsulfone (byproduct by excess oxidation): 7%.
LC/MS of titled compound; Exact Mass: 140.0, measured value (positive): 141.1
LC/MS of byproduct; Exact Mass: 156.0, measured value (positive): 157.1

COMPARATIVE EXAMPLE 9

Production of 5-trifluoromethylthiopentyl-[4-chloro-2-fluoro-5-(2,2,2-trifluoroethylsulfinyl)phenyl] ether

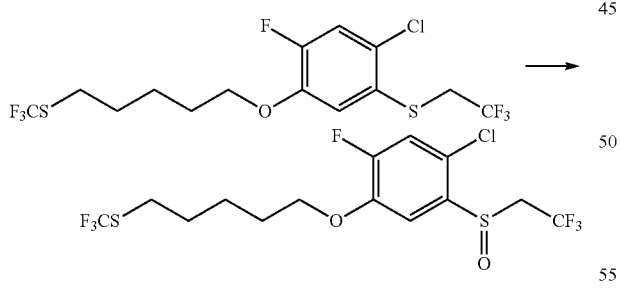

(1) Production of Titled Compound 5-trifluoromethylthiopentyl-[4-chloro-2-fluoro-5-(2,2,2-trifluoroethylthio)phenyl] ether (215.4 mg, 0.500 mmol) was dissolved in acetonitrile (1.0 mL). Sodium tungstate dihydrate (8.2 mg, 0.025 mmol) was added thereto. While stirring the mixture at room temperature, 30% hydrogen peroxide (113.4 mg, 1.0 mmol) was added thereto. The mixture was stirred at room temperature for 15 h. The organic layer of the reaction mixture was analyzed by HPLC (area percentage). As a result, the components excluding the solvent etc. in the reaction mixture were as follows;
5-trifluoromethylthiopentyl-[4-chloro-2-fluoro-5-(2,2,2-trifluoroethylsulfinyl)phenyl] ether (titled compound): 61%,
5-trifluoromethylthiopentyl-[4-chloro-2-fluoro-5-(2,2,2-trifluoroethylthio)phenyl]ether (starting compound): 32%,
5-trifluoromethylthiopentyl-[4-chloro-2-fluoro-5-(2,2,2-trifluoroethylsulfonyl)phenyl]ether (byproduct by excess oxidation): 2%.

(2) Production of Titled Compound Using Additional Hydrogen Peroxide

To the reaction mixture obtained above, 30% hydrogen peroxide (113.4 mg, 1.0 mmol) was added. The mixture was stirred at room temperature for 23 h. The organic layer of the reaction mixture was analyzed by HPLC (area percentage). As a result, the components excluding the solvent etc. in the reaction mixture were as follows;
5-trifluoromethylthiopentyl-[4-chloro-2-fluoro-5-(2,2,2-trifluoroethylsulfinyl)phenyl] ether (titled compound): 79%,
5-trifluoromethylthiopentyl-[4-chloro-2-fluoro-5-(2,2,2-trifluoroethylthio)phenyl]ether (starting compound): 0%,
5-trifluoromethylthiopentyl-[4-chloro-2-fluoro-5-(2,2,2-trifluoroethylsulfonyl)phenyl]ether (byproduct by excess oxidation): 12%.

INDUSTRIAL APPLICABILITY

As disclosed in Patent Document 1, the sulfoxide derivative represented by the general formula (1) has excellent acaricidal activity.

According to the present invention, a novel industrially preferable method for producing a sulfoxide derivative represented by the general formula (1), which is useful as an agricultural chemical such as an acaricide is provided. As described above in the present specification, the method of the present invention is economical, environmentally friendly and has high industrial utility value. Particulary by using the method of the present invention, it is possible to selectively produce a desired sulfoxide derivative by avoiding excess oxidation to the sulfone derivative. Therefore, the present invention has an advantage that there is no need to remove byproduct sulfone derivatives which are difficult to remove.

In short, the present invention has high industrial applicability.

The invention claimed is:

1. A method for producing a sulfoxide derivative represented by general formula (1):

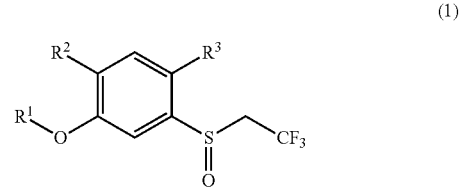

(1)

(wherein,
R¹ is a C1 to C10 alkyl group,
a C3 to C6 cycloalkyl C1 to C6 alkyl group, wherein the said C3 to C6 cycloalkyl group moiety may be monosubstituted or polysubstituted by a halogen atom, a C1 to C4 alkyl group, a C1 to C4 alkoxy group or C1 to C4 haloalkyl group,
a phenyl C1 to C6 alkyl group, wherein the said phenyl group moiety may be monosubstituted or polysubstituted by a halogen atom, a C1 to C4 alkyl group, a C1 to C4 alkoxy group, a C1 to C6 haloalkyl group, a cyano group or a nitro group,
a C1 to C4 alkoxy C2 to C10 alkyl group,
a C1 to C4 haloalkoxy C2 to C10 alkyl group,
a C1 to C4 alkylthio C2 to C10 alkyl group,
a C1 to C4 alkylsulfinyl C2 to C10 alkyl group,
a C1 to C4 alkyl sulfonyl C2 to C10 alkyl group,
a C1 to C4 haloalkylthio C2 to C10 alkyl group,
a C1 to C4 haloalkylsulfinyl C2 to C10 alkyl group,
a C1 to C4 haloalkylsulfonyl C2 to C10 alkyl group,
a C1 to C6 haloalkyl group,
a C3 to C6 cycloalkyl C1 to C6 haloalkyl group wherein the said C3 to C6 cycloalkyl group moiety may be monosubstituted or polysubstituted by a halogen atom, a C1 to C4 alkyl group, a C1 to C4 alkoxy group or a C1 to C6 haloalkyl group,
a phenyl C1 to C6 haloalkyl group, wherein the said phenyl moiety may be monosubstituted or polysubstituted by a halogen atom, a C1 to C4 alkyl group, a C1 to C4 alkoxy group, a C1 to C4 haloalkyl group, a cyano group or a nitro group, or
a C1 to C4 haloalkylthio C1 to C6 haloalkyl group;
$R^2$ and $R^3$ are each independently a hydrogen atom, a halogen atom or a C1 to C4 alkyl group), which comprises reacting a sulfide derivative represented by general formula (2):

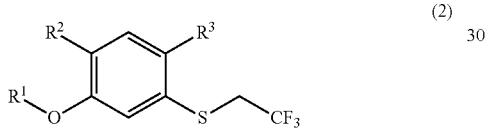
(2)

(wherein, $R^1$, $R^2$ and $R^3$ are as defined above) with an oxidizing agent in the presence of both a catalyst which is a metal-ligand complex containing a metal compound and
a ligand compound represented by general formula (3):

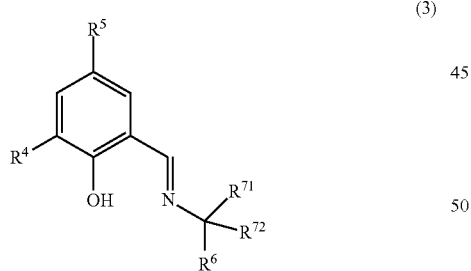
(3)

which is selected from the group consisting of

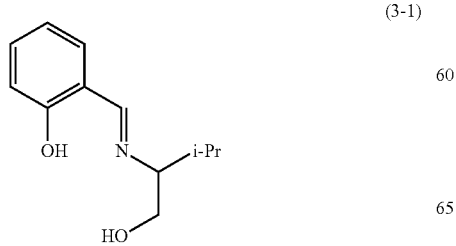
(3-1)

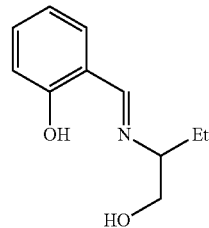
(3-2)

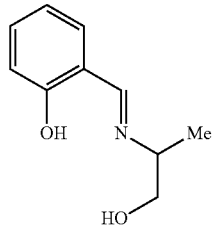
(3-3)

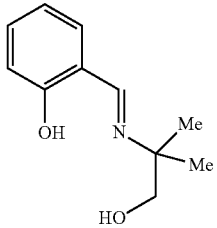
(3-4)

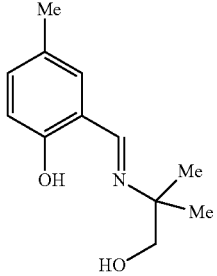
(3-6)

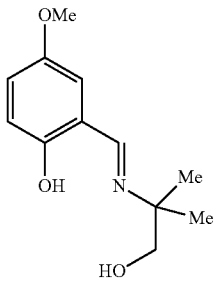
(3-7)

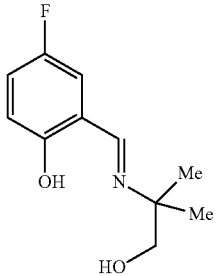
(3-8)

-continued (3-9)
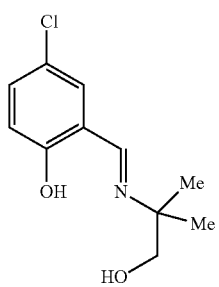

(3-10)
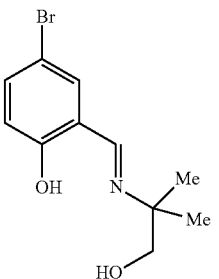

(3-11)
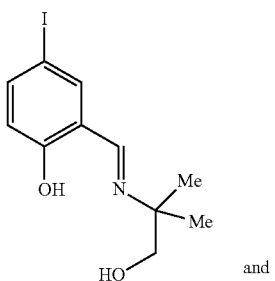

(3-12)
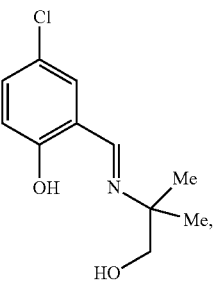

and
a benzoic acid compound represented by general formula (4):

(4)
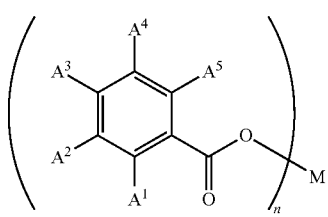

(wherein,
$A^1$ is a C1 to C2 alkoxy group;
$A^2$ is a hydrogen atom;
$A^3$ is a hydrogen atom or a C1 to C2 alkoxy group;
$A^4$ is a hydrogen atom;
$A^5$ is a C1 to C2 alkoxy group;
M is a hydrogen atom, an alkali metal atom or an alkaline earth metal atom; and
n is 1 or 2).

2. The method according to claim 1, wherein
$R^1$ is a C1 to C10 alkyl group,
a C3 to C6 cycloalkyl C1 to C6 alkyl group, wherein the said C3 to C6 cycloalkyl group moiety may be monosubstituted or polysubstituted by a halogen atom or a C1 to C4 alkyl group,
a phenyl C1 to C6 alkyl group, wherein the said phenyl group moiety may be monosubstituted or polysubstituted by a halogen atom or a C1 to C4 alkyl group,
a C1 to C4 alkoxy C2 to C10 alkyl group,
a C1 to C4 haloalkoxy C2 to C10 alkyl group,
a C1 to C4 alkylthio C2 to C10 alkyl group,
a C1 to C4 alkylsulfinyl C2 to C10 alkyl group,
a C1 to C4 alkylsulfonyl C2 to C10 alkyl group,
a C1 to C4 haloalkylthio C2 to C10 alkyl group,
a C1 to C4 haloalkylsulfinyl C2 to C10 alkyl group,
a C1 to C4 haloalkylsulfonyl C2 to C10 alkyl group,
a C1 to C6 haloalkyl group,
a C3 to C6 cycloalkyl C1 to C6 haloalkyl group, wherein the said C3 to C6 cycloalkyl group moiety may be monosubstituted or polysubstituted by a halogen atom or a C1 to C4 alkyl group, or a phenyl C1 to C6 haloalkyl group, wherein the said phenyl group moiety may be monosubstituted or polysubstituted by a halogen atom or a C1 to C4 alkyl group.

3. The method according to claim 1, wherein
$R^1$ is a C1 to C10 alkyl group,
a C1 to C4 alkoxy C2 to C10 alkyl group,
a C1 to C4 haloalkoxy C2 to C10 alkyl group,
a C1 to C4 alkylthio C2 to C10 alkyl group,
a C1 to C4 alkylsulfinyl C2 to C10 alkyl group,
a C1 to C4 alkylsulfonyl C2 to C10 alkyl group,
a C1 to C4 haloalkylthio C2 to C10 alkyl group,
a C1 to C4 haloalkylsulfinyl C2 to C10 alkyl group,
a C1 to C4 haloalkylsulfonyl C2 to C10 alkyl group, or
a C1-C6 haloalkyl group.

4. The method according to claim 1, wherein $R^1$ is a C1 to C4 haloalkylthio C2 to C10 alkyl group; and $R^2$ and $R^3$ are each independently a halogen atom or a C1 to C4 alkyl group.

5. The method according to claim 1, wherein $R^1$ is a 5-trifluoromethylthiopentyl group or a 6-trifluoromethylthiohexyl group; and either $R^2$ is a fluorine atom and $R^3$ is a chlorine atom, or $R^2$ and $R^3$ are methyl groups.

6. The method according to claim 1, wherein $R^1$ is a 5-trifluoromethylthiopentyl group; $R^2$ is a fluorine atom; and $R^3$ is a chlorine atom.

7. The method according to claim 1, wherein $R^1$ is a 6-trifluoromethylthiohexyl group; and $R^2$ and $R^3$ are methyl groups.

8. The method according to claim 1, wherein the metal compound is an iron compound.

9. The method according to claim 1, wherein
a ligand compound represented by general formula (3):

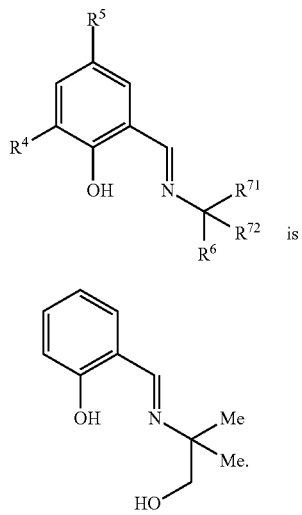

is

10. The method according to claim 1, wherein M is an alkali metal atom; and n is 1.

11. The method according to claim 1, wherein M is a sodium atom; and n is 1.

12. The method according to claim 1, wherein
$A^1$ is a methoxy group;
$A^2$ is a hydrogen atom;
$A^3$ is a hydrogen atom or a methoxy group;
$A^4$ is a hydrogen atom;
$A^5$ is a methoxy group;
M is a sodium atom; and n is 1.

13. The method according to claim 1, wherein
$A^1$ is a methoxy group;
$A^2$ is a hydrogen atom;
$A^3$ is a hydrogen atom;
$A^4$ is a hydrogen atom;
$A^5$ is a methoxy group;
M is a sodium atom; and n is 1.

14. The method according to claim 1, wherein
$A^1$ is a methoxy group;
$A^2$ is a hydrogen atom;
$A^3$ is a methoxy group;
$A^4$ is a hydrogen atom;
$A^5$ is a methoxy group;
M is a sodium atom; and n is 1.

* * * * *